United States Patent [19]

Kauvar et al.

[11] Patent Number: 5,786,336
[45] Date of Patent: Jul. 28, 1998

[54] TARGET-SELECTIVE PROTOCOLS BASED ON MIMICS

[75] Inventors: Lawrence M. Kauvar, San Francisco; Matthew H. Lyttle, Point Reyes Station; Amy S. Morgan, Oakland, all of Calif.; Richard F. Borch, Pittsford, N.Y.

[73] Assignee: Terrapin Technologies, Inc., South San Francisco, Calif.

[21] Appl. No.: 305,993

[22] Filed: Sep. 19, 1994

Related U.S. Application Data

[63] Continuation-in-part of Ser. No. 130,736, Oct. 1, 1993, Pat. No. 5,545,621, and Ser. No. 126,229, Sep. 24, 1993, Pat. No. 5,599,903, which is a continuation-in-part of Ser. No. 863,564, Apr. 3, 1992, abandoned, which is a continuation-in-part of Ser. No. 693,245, Apr. 29, 1991, abandoned.

[51] Int. Cl.$^6$ .............................. A61K 38/06; C07K 5/08
[52] U.S. Cl. ............................................. 514/18; 530/331
[58] Field of Search ................................. 514/18; 530/331

[56] References Cited

U.S. PATENT DOCUMENTS

| | | |
|---|---|---|
| 4,851,388 | 7/1989 | Bright . |
| 4,963,263 | 10/1990 | Kauvar ................................... 210/635 |
| 5,133,866 | 7/1992 | Kauvar ................................... 210/635 |
| 5,204,241 | 4/1993 | Pero . |
| 5,430,045 | 7/1995 | Goldberg et al. . |

FOREIGN PATENT DOCUMENTS

| | | |
|---|---|---|
| 0 480 061 | 4/1992 | European Pat. Off. . |
| 1 317 275 | 5/1973 | United Kingdom . |
| WO 86/00991 | 7/1985 | WIPO . |
| WO 90/12088 | 4/1990 | WIPO . |
| WO 91/17240 | 5/1991 | WIPO . |
| WO 92/00320 | 1/1992 | WIPO . |
| WO 92/19767 | 4/1992 | WIPO . |

OTHER PUBLICATIONS

Castro, et al., "Differences Among Human Tumor Cells in the Expression of Glutathione Transferases and Other Glutathione-Linked Enzymes" *Oxford University Press*, 1569–1576 (1990).

Held, et al. "Effect of Dimethyl Fumarate on the Radiation Sensitivity of Mammalian Cells in Vitro" *Radiation Research* 115, 495–502 (1988).

Houghton Mifflin Company *Webster's II New Riverside University Dictionary*, 849 (1988).

Mannervik, et al. "Identification of Three Classes of Cytosolic Glutathione Transferase Common to Several Mammalian Species: Correlation Between Structural Data and Enzymatic Properties" *Proc. Natl. Acad. Sci. USA*, vol. 82, pp. 7202–7206 (1985).

Mozer et al., "Purification and Characterization of Corn Glutathione S–Transferase", *Biochemistry* 22:1068–1072 (1983).

Puchalski, et al. "Expression of Recombinant Glutathione S–Transferase π, Ya, or $Yb_1$ Confers Resistance to Alkylating Agents" *Proc. Natl. Acad. Sci., USA* vol. 87, pp. 2443–2447 (1990).

Ricci, et al. "Detection of Glutathione Transferase Activity on Polyacrylamide Gels" *Analytical Biochemistry* 143, 226–230 (1984).

Schisselbauer et al. "Characterization of Glutathione S–Transferase Expression in Lymphocytes From Chronic Lymphocytic Leukemia Patients" *Cancer Research* 50, 3562–3568 (1990).

Sheh, et al. "Synthesis of Cyclic Peptide Homologs of Glutathione as Potential Antitumor Agents" *Int. J. Peptide Protein Res.* 35, 55–62 (1990).

Smith, et al. "Denitrosation of 1,3–Bis(2–chloroethyl)–1–nitrosourea by Class Mu Glutathione Transferases and Its Role in Cellular Resistance in Rat Brain Tumor Cells" *Cancer Research* 49, 2621–2625 (1989).

Takeo, et al. "Binding Constants of Dextrans and Isomaltose Oligosaccharides to Dextran–Specific Myeloma Proteins Determined by Affinity Electrophoresis" *The Journal of Immunology*, vol. 121, 2305–2310 (1978).

Tew, et al. "Ethacrynic Acid and Piriprost as Enhancers of Cytotoxicity in Drug Resistant and Sensitive Cell Lines" *Cancer Research* 48, 3622–3625 (1988).

Vos, et al. "Differential Induction of Rat Hepatic Glutathione S–Transferase Isoenzymes by Hexachlorobenzene and Benzyl Isothiocyanate" *Biochemical Pharmacology*, vol. 37, No. 6, pp. 1077–1082 (1988).

(List continued on next page.)

*Primary Examiner*—Christine M. Nucker
*Assistant Examiner*—Benet Prickril
*Attorney, Agent, or Firm*—Morrison & Foerster LLP

[57] ABSTRACT

A method to potentiate the effect of a chemotherapeutic agent in a tumor cell, which method comprises administering to said tumor cell, along with said chemotherapeutic agent, a potentiating amount of a compound of the formula:

$$Y-CO-NHCHCO-AA_C; \quad (1)$$
$$| $$
$$CH_2-SX$$

or an amide, ester or hybrid amide/ester thereof, wherein X is a hydrocarbon radical optionally substituted on any aromatic moiety contained therein; Y—CO is γ-Glu or β-Asp and $AA_C$ is an amino acid, preferably glycine, phenylglycine, β-alanine, alanine or phenylalanine is disclosed.

Similar compounds can also be used to selectively exert cytotoxicity versus target cells as compared to nontarget cells and also to elevate the production of GM progenitors in bone marrow of mammalian subjects.

5 Claims, 3 Drawing Sheets

OTHER PUBLICATIONS

Waxman "Glutathione S–Transferases: Role in Alkylating Agent Resistance and Possible Target for Modulation Chemotherapy—A Review" *Cancer Research* 50, 6449–6454 (1990).

Wiencke et al. "Human Glutathione S–Transferase Deficiency as a Market of Susceptibility to Epoxide–Induced Cytogenic Damage" *Cancer Research* 50, 1585–1590 (1990).

Adang, A.E.P. et al., The Glutathione–Binding Site in Glutathione S–Transferase, Biochem J. (1990) 269:47–54.

Principato, G.B., et al., Effects of Some S–Blocked Glutathione Derivatives on the Prevalent Glyoxalase II (a Form) of Rat Liver, Enzyme (1989) 41:175–180.

Morris, D., Synthesis of the α–and γ–Isomers of Glutamylcystinylvaline, Biochem J. (1960) 76:349–353.

Helgestad et al. (1986) Vitamin C and thiol reagents promote the in–vitro growth of murine granulocyte–macrophage progenitor cells. *Blut* 52, 1–8. see abstract.

TARGET-SELECTIVE PROTOCOLS BASED ON MIMICS

This application is a continuation-in-part of U.S. Ser. No. 08/126,229, filed Sep. 24, 1993, now issued as U.S. Pat. No. 5,599,903, which is a continuation-in-part of U.S. Ser. No. 07/863,564, filed Apr. 3, 1992, now abandoned, which is a continuation-in-part of U.S. Ser. No. 07/693,245, filed Apr. 29, 1991, now abandoned. This application is a continuation-in-part of U.S. Ser. No. 08/130,736, filed Oct. 1, 1993, now issued as U.S. Pat. No. 5,545,621. The disclosures of all the foregoing applications are incorporated herein by reference.

TECHNICAL FIELD

The invention relates to methods to exert desired selective pharmacological effects using certain tripeptide compounds which are analogs of glutathione. In particular, the invention concerns selectively potentiating chemotherapeutic agents, selectively exerting cytotoxic effects on target cells and stimulation of production of GM progenitors in bone marrow of mammalian subjects.

BACKGROUND ART

Glutathione (GSH), in its reduced form, is a tripeptide of the formula: γ-Glu-Cys-Gly. Reduced glutathione has a central role in maintaining the redox condition in cells and is also an essential substrate for glutathione S-transferase (GST) which facilitates the detoxification of foreign substances by a number of mechanisms, including catalysis of the coupling of an electrophilic portion of a toxin, for instance, to glutathione, rendering the toxin more susceptible to clearance. A second mechanism, which also involves glutathione as substrate, resides in the reduction of peroxides with the concomitant oxidation of glutathione.

Adang, A. E. P., et al., *Biochem J* (1990) 269:47–54, described tripeptide analogs of GSH which interact with various GST isoenzymes at different concentrations. These analogs are modified forms of GSH in which at least one of the glycine, cysteine, or gamma-glutamine residues is replaced by an alternate amino acid residue.

Additional modified forms have been disclosed, for example, by Principato, G. B., et al., *Enzyme* (1989) 41:175–180, who studied the effect of a tripeptide GSH analog on glyoxalase II enzyme of rat liver. The tripeptide used by this group was of the formula γ-Glu-ρ-chlorophenylcarbonylmethyl-Cys-Ser. Morris, D., in *Biochem J* (1960) 76:349–353, described the synthesis of γ-Glu-benzyl-Cys-Val. A large number of GSH tripeptide analogs containing a substitution for only one of the three GSH amino acids have been reported and are commercially available.

The invention described hereinbelow concerns protocols that take advantage of the selectivity of glutathione tripeptide analogs which are also useful as affinity ligands on chromatographic supports and as members of panels which are used to characterize the various isoenzymes of glutathione-S-transferase. Glutathione-S-transferases (GSTs) are present in the form of a number of isoenzymes which differ in specific binding abilities, in substrate and inhibitor specificities and in tissue distribution. Particular complements of GST isoenzymes, with their accompanying differences in properties, thus are characteristic of specific tissues or cell types, such as tumor tissues. As GST is central to the overall metabolism of the tissue or cell as it relates to its defense against toxic substances, the character of the complement of the GST for the cell or tissue is important in designing strategies either for the destruction of the cell or tissue, as would be desirable for tumor cells, or for enhancement of its metabolic function, as would be the case for normal tissue.

The various GST isoenzymes are dimeric proteins formed by binary combinations of monomers encoded by at least fifteen known genes in four gene families resulting in the theoretical possibility of several dozen different dimers, even allowing for preferential dimerization of monomers from the same gene family. In addition to the variability that arises from these combinatorial possibilities, the GST isoenzyme subunits are polymorphic in the human population and have been considered to be subject to additional variation due to gene conversion events among the tandemly repeated members of the family. Posttranslational modifications add further to this variability. As each cell or tissue may contain one or several of these theoretically possible enzymes, determination of the GST complement is of great importance.

The present invention, by providing glutathione analogs which are useful as sorbents and as solution phase inhibitors, as well as panels that include them, offers improved methods to characterize and manipulate individual GST enzymes or sets thereof.

DISCLOSURE OF THE INVENTION

The invention is directed to methods and protocols which take advantage of the selectivity of the tripeptide glutathione analogs of the invention for the various GST isoenzymes. By taking account of the GST isoenzyme levels in targeted cells as compared to nontargeted cells, the appropriate glutathione analog can be selected to exert a selective cytotoxic effect or to selectively potentiate a chemotherapeutic agent. In addition, the analogs of the invention are able to stimulate and potentiate bone marrow in mammalian subjects. It has further been found that in order to exert intracellular effects, the compounds of the invention are preferably supplied as the diamides or diesters or hybrids thereof. Thus, in one aspect, the invention is directed to a method to potentiate the effect of a chemotherapeutic agent in a tumor cell, which method comprises administering to said tumor cell, along with said chemotherapeutic agent, a potentiating amount of a diester or diamide of a compound of the formula:

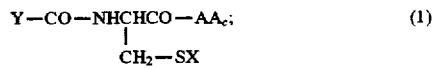

(1)

or an amide, ester or hybrid amide/ester thereof, wherein X is a hydrocarbon radical optionally substituted on any aromatic moiety contained therein; Y—CO is γ-Glu or β-Asp and AA$_C$ is an amino acid; preferably glycine, phenylglycine, β-alanine, alanine or phenylalanine.

In a second aspect, the invention is directed to exert a cytotoxic effect on target cells as compared to nontarget cells which method comprises identifying the GST isoenzymes whose levels are elevated in said target cells as compared to nontarget cells;

selecting a compound of the formula:

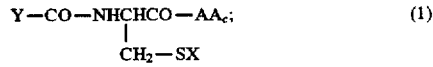

(1)

wherein X; Y—CO and AA$_C$ are as defined above which selectively inactivates said isoenzyme; and administering said delected compound or an amide, ester or hybrid amide/ester thereof, to said target cells in an amount toxic to said target cells in comparison to said nontarget cells.

In a third aspect, the invention is directed to stimulate the production of granulocyte macrophage (GM) progenitors in the bone marrow of a subject which method comprises administering to said subject an effective amount of a compound of the formula:

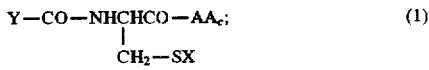

(1)

or an amide, ester or hybrid amide/ester thereof, wherein X; Y—CO and $AA_C$ are as defined above.

In other aspects, the invention is also directed to the diamides and diesters useful in the above-described methods.

BRIEF DESCRIPTION OF THE DRAWINGS

FIG. 4 shows the dose-response relationship of stimulation of GM progenitors by administration of benzyl-PG.

MODES OF CARRYING OUT THE INVENTION

Figure 1:
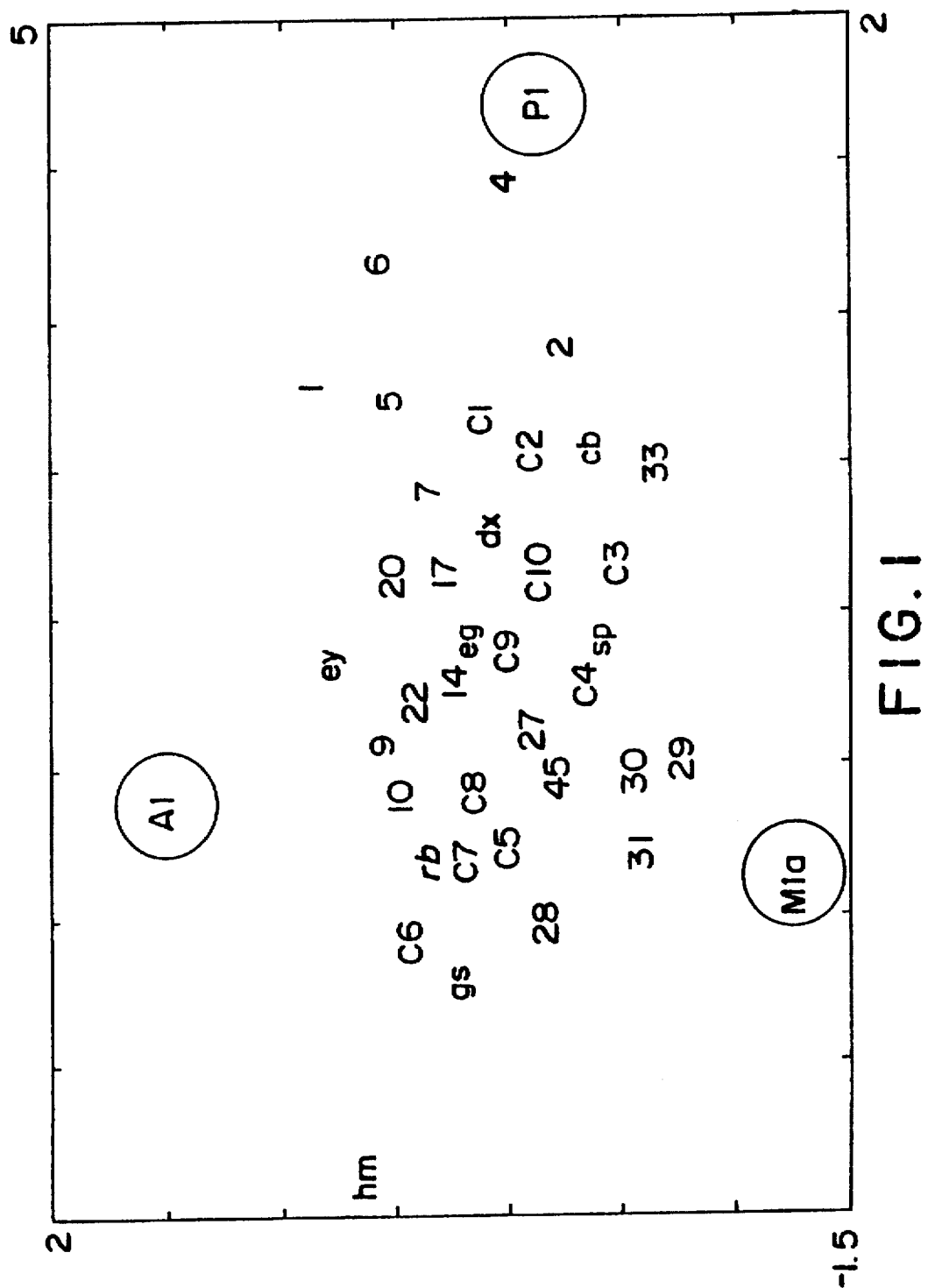
FIG. 1 Multivariate analysis of GST inhibitors. Inhibitor quality is visualized by plotting potency against each of three recombinant human GST isoenzymes (A1—1, M1a—1a, and P1—1) and projecting the points onto a plane defined by the principal components of the distribution. Target values for ideal inhibitors of each isozyme are denoted by circles labeled with the isozyme name; the criteria for an ideal inhibitor are 100-fold specificity and $K_i=0.1$ μM. Three families of compounds presented in Example 9 are compared: a selection of paralogs from Table 5 (numbers), a series of n-alkyl GSH analogs from Table 7 ($C_n$ in boldface), and a selection of the small organic molecules from Table 7 (italics). For purposes of clarity, certain data are not plotted, namely, those for compounds of low specificity, which are clustered at the center of the plot.
Figure 1A:
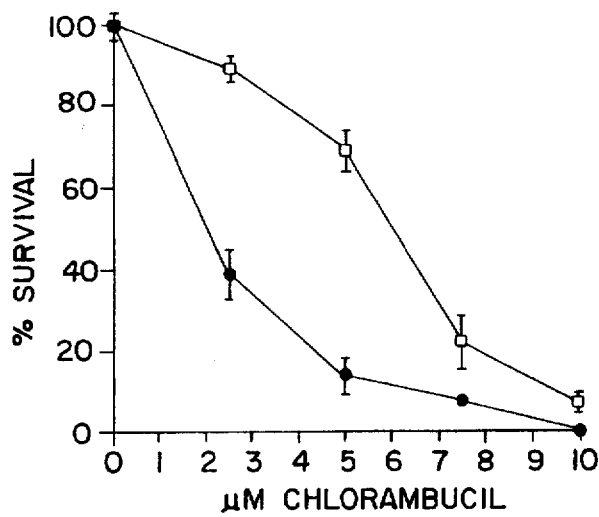
Figure 1B:
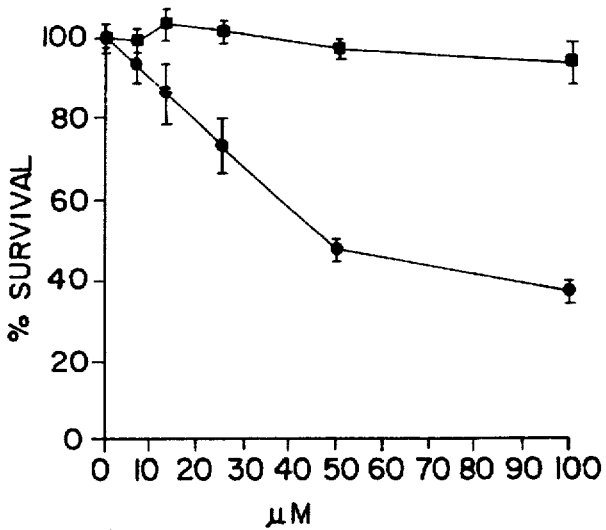

The compounds of the invention potentiate the toxicity of chemotherapeutic agents, while, at the same time, apparently potentiating the protective effects of bone marrow. Specifically, it has been established that administration of the compounds of the invention enhance the production of granulocyte macrophage (GM) progenitors. In view of this effect, not only is the toxicity of the chemotherapeutic agent toward tumor cells enhanced, but normal cells are better protected vis-à-vis the chemotherapeutic agent. Further, the compounds of the invention may be useful in treating various bone marrow related deficiencies such as anemia.

The compounds from which reagents that show selectivity for various GST isoenzymes are selected are a set of tripeptide glutathione analogs. These compounds, as set forth hereinbelow, provide a range of selectivity for the various isoenzymes. This makes appropriate members of this class useful for chromatographic separations of the isoenzymes, selective research reagents in manipulating GSTs, and selective active ingredients in procedures to target particular cells either with respect to a direct cytotoxic effect or by potentiating other chemotherapeutic agents.

When tested by affinity chromatography several of these diverse sorbents selectively bind mammalian GST isoenzymes of a particular class or classes according to the following classification scheme proposed by Mannervik, B., et al., Proc Natl Acad Sci (1985) 82:7202–7206: Alpha (e.g., human α and A1—1, rat 1—1 and 2—2), Mu (human μ, M1a—1a, rat 3—3 and 4—4), Pi (human π and P1—1, rat 7—7) and, a more recently proposed class, Theta (rat 5—5). When tested for inhibition of GST enzymatic activity, several sorbents also act as selective or specific inhibitors of GST isoenzyme classes. Therefore, the compounds, panels and methods of this invention enable strategies for the design of drugs targeting cells with elevated levels of particular GST isoenzymes.

The Compounds of the Invention

The compounds of the invention include the moiety of formula 1, wherein X is a hydrocarbon (1–20C) radical wherein any aromatic moiety contained within the hydrocarbon radical may optionally be substituted as described below. Preferred embodiments for X include methyl, propyl, hexyl, octyl, benzyl, naphthyl and trityl, in particular hexyl, heptyl, octyl, benzyl and naphthyl.

As used herein, "hydrocarbon radical" refers to a straight or branched chain or cyclic, saturated or unsaturated, aliphatic or aromatic hydrocarbyl residue containing 1–20C. Representative of such substituents include methyl, ethyl, propyl, isopropyl, butyl, tertiary butyl, hexyl, octyl, nonyl, 2,3-dimethyloctyl, dodecyl, 9,9-dimethylundecyl, allyl, 2-butenyl, isobutenyl, cyclohexyl, cyclopentyl, cycloheptyl, phenyl, benzyl, 4-methylbenzyl, triphenylmethyl, methoxyethyl, ethylthioethyl, diethylaminopropyl and the like. Also included in hydrocarbyl groups suitable for X are bicyclic aryl (1–20C) moieties including naphthyl.

In some instances, as indicated in the examples above, the hydrocarbon radical may contain heteroatom substituents or interspersed heteroatoms such as Cl, Br, N, O and the like.

$AA_C$ may be any gene-encoded amino acid. $AA_C$ may also be an amino acid residue which is not encoded by the gene, such as hydroxyproline (HP), 4-aminobutyric acid (4ABu), β-alanine (β-ala or βA), phenylglycine (PG or φG), and the like. Preferred embodiments of $AA_C$ include glycine, phenylglycine, alanine and phenylalanine. $AA_C$ is bound to the remainder of the compound of formula 1 through a peptide bond.

In the compounds of the invention, substitution of phenylglycine for Gly, increasing the hydrophobicity and bulk of this site, results in high specificity for π-class isoenzymes (e.g., rat 7—7). The use of Ala and β-Ala at the Gly site produces sorbents with high specificity for μ-class isoenzymes (e.g., rat 3—3 and 4—4). The shift from Ala to β-Ala, an alteration that increases the length of the backbone, results in differential binding of different μ-class isoenzymes.

For compounds of the invention wherein X is substituted benzyl, whether in the form of the free acid or salt of formula 1 or as esters, amides, hybrids, or cycloamido forms, specificity for various subtypes of human GSTs can be controlled by varying the para substituent on the benzyl moiety. Embodiments of X which contain hydrophobic para substituents such as t-butyl or methyl or benzyl, bind preferentially to human GSTs of the μ (M1) class, such as GST-M1a—1a. Electron withdrawing substituents at the para position, such as nitro or chloro preferably bind π (P1—1) enzymes. Plots of Hammett sigma/meta values against the log fraction of isoenzyme bound show a linear correlation but no clear correlation appears when sigma/para values are used. Some steric bulk appears necessary to bind GSTs generally; benzyl substituents which are unsubstituted or contain only fluoride substitutions do not bind appreciably.

For compounds of the invention wherein X is an unsubstituted hydrocarbyl (1–20C) moiety, whether in the form of the free acid or salt of formula 1 or as esters, amides, mixed ester/amides or cycloamido forms, specificity for various subtypes of human GSTs can be controlled by varying the hydrophobicity of the substituent on the sulfur atom of the Cys moiety, for instance, the length of n-alkyl adducts. Generally, the binding strength for GSTs increases with the chain length of the alkyl group, but there is a change in isoenzyme selectivity with increasing chain length. Embodiments of X which contain S-alkyl chains of three or four atoms inhibit preferentially human GSTs of the μ class, particularly GST-M1a—1a. In the range of alkyl groups containing five to eight carbons, human GSTs of the α and μ classes are inhibited to about the same extent and are selectively inhibited as compared to human π-class isoenzyme. Finally, for S-nonyl and S-decyl GSH derivatives, human GSTs from all three classes are inhibited to about the same extent.

The compounds of the invention may include the alkyl, alkenyl or arylalkyl esters or alkyl-type, alkenyl-type or arylalkyl-type amides, or may be in the amidocyclic forms. Alkyl-type esters of the free carboxyls are esters of the straight- and branched-chain and cyclic alkyl alcohols (1–10C) such as methanol, ethanol, isopropanol, t-butanol, n-hexanol and the like. The carbon chain of the alkyl-type alcohol may be interrupted by one or two nonadjacent heteroatoms, i.e., N, O or S. For example, alkyl-type alcohols include N,N-dimethylethanolamine and 2-(1-hydroxy-2-ethyl)-4,4,6-trimethyltetrahydro-1,3-oxazine. Suitable alkyl-type (1–10C) amides are those of primary straight- or branched-chain or cyclic alkyl amines, such as methylamine, ethylamine, n-propylamine, isopentylamine, and isohexylamine. These carbon chains also may be interrupted by one or two nonadjacent heteroatoms, i.e., N, O or S. Alkenyl-type esters and amides are prepared from the corresponding amines which contain at least one double bond. Arylalkyl-type esters may contain 7–12C and include, phenyl-lower alkyl derivatives such as benzyl, 2-phenylethyl, 2-phenylpropyl, and the like. The phenyl group may be unsubstituted or may be substituted with 1–2 substituents, such as methyl, chloro and the like which do not materially effect the properties of the invention compounds. Again, the hydrocarbon chain may be interrupted with 1 or 2 heteroatoms, and heterocyclic aromatic systems also may be included. The esters and amides are prepared using conventional techniques, with suitable protection of any alcohol or amino functional groups in the substrate compound of formula 1.

It should be noted that the compounds may be prepared as either the mono- or diesters or the mono- or diamides (or triesters or triamides, depending on the choice of $AA_C$). Thus, the invention includes esters wherein only one of the carboxyl groups is esterified, where two carboxyl groups are esterified or where all carboxyl groups (if more than two) are esterified. Similar embodiments are applicable to the corresponding amides. In addition, the compounds may be prepared as mixed esters/amides wherein one carboxyl is an ester and another an amide.

Salts of the compounds of the invention may be formed of inorganic bases such as sodium or potassium hydroxide or of organic bases such as caffeine or piperidine to form the basic salts of the free carboxyl groups or may be formed from organic or inorganic acids to obtain the acid addition salts of free amino groups. Thus, the salts may be of inorganic bases such as sodium hydroxide, calcium hydroxide, ammonium hydroxide, magnesium hydroxide, and the like, or of organic bases such as trimethylamine, pyridine, pyrimidine, lysine, caffeine, and the like. The acid addition salts may be formed from inorganic acids such as hydrochloric acid, hydrobromic acid, sulfuric acid, phosphoric acid, and the like, or from organic acids such as acetic acid, propionic acid, glycolic acid, pyruvic acid, oxalic acid, malic acid, tartaric acid, citric acid, benzoic acid, cinnamic acid, mandelic acid, salicylic acid, and the like.

Salts are formed in standard protocols by treating with the appropriate base or acid at a temperature of from about 0° C. to about 100° C., preferably at room temperature either in water alone or in combination with an inert water-miscible organic solvent such as methanol, ethanol or dioxane.

Cyclic forms of the compound of formula 1 are prepared by bridging free amino and free carboxyl groups contained in the substrate compound. Formation of the cyclic compounds is conducted conventionally by treatment with a dehydrating agent such dicyclohexyl carbodiimide by means known in the art per se, with suitable protection if needed.

In most embodiments of the compounds of formula 1, the cycloamide is formed between the free amino group present at the amino terminus on Y with the carboxyl group at the carboxy terminus represented by $AA_C$. However, in those limited embodiments wherein $AA_C$ contains a side-chain amino group (such as those wherein $AA_C$ is lysine) alternative forms of the cycloamido compounds may also be prepared involving the side-chain amine of $AA_C$ and the side-chain carboxyl of Y. Suitable protecting groups can be used to direct the cycloamidation as is known in the art.

The various substituents designated by X can be noted by standard abbreviations, and their inclusion in the tripeptide analogs of the compounds of the invention is symbolized by C(X).

The notation for $AA_C$ may also be in the standard one-letter amino acid abbreviation code or other suitable abbreviation for non-gene encoded amino acids.

Thus, using this notation, suitable compounds of formula 1 include:

γE-C(Bz) (Me)-G,
βD-C(Trt)-A, γE-C(p-ClBz)-G,
γE-C(Pr) (Me)-V, γE-C(p-NO₂Bz)-PG,
βD-C(Hx)-PG, γE-C(p-MeBz)-V,
γE-G-C(Bz)-4ABu, γE-C(p-BuBz)-βA,
D-B-C(Hx)-F, γE-C(p-MeOBz)-βA,
γE-C(Hx)(Me)-N, γE-C(p-EtSBz)-PG,
γE-C(Trt)-N, γE-C(p-Me₂N-Bz)-βA,
γE-C(o-BuBz)-PG
and the like.

These compounds of formula 1 are cyclized or esterified/amidated to obtain the compounds of the invention.

Features of the Invention Compounds

The compounds of the invention are useful as solution-phase or immobilized inhibitors of enzymes, such as glutathione-S-transferases (GSTs), which utilize glutathione as substrates. Such inhibition may be desirable both in analytical and therapeutic contexts.

As therapeutic agents, the esterified compounds of the invention are most useful since permeation of the cell membrane is best achieved by these less hydrophilic forms.

Suitable amides or ester/amide hybrids may thus also be used. Particularly preferred esters are the benzyl esters and derivatized benzyl esters. Also preferred are the ethyl esters.

However, the intracellular effects are believed due to the generation of the unesterified forms of the compounds of the invention.

Since the compounds of the invention are dicarboxylic acids, the diesters are the preferred form. In some instances, metabolism appears to proceed through the monoester; nevertheless, the active form is believed to be the unesterified form intracellularly. However, uptake of glutathione per se appears to be inhibited by esterification as described by Welner, W. P. et al. *Proc Natl Acad Sci USA* (1984) 81:4732–4735; Anderson, M. E. et al. *Arch Biochem Biophys* (1985) 239:538–548; Tsan, M.-F., et al. *J App Physiol* (1989) 66:1029–1034. Possibly this is due to utilization of amino acid uptake channels for glutathione itself. On the other hand, Lo, T. W. C. et al. *Biochem Pharmacol* (1992) 44:2357–2363 found that diethyl esters of glyoxalase inhibitors were able to permeate tumor cells.

Thus, for use in in vitro cell culture, for example in screening assays, the preferred compounds of the invention are the esterified forms. This is shown dramatically with respect to toxicity against HT-29 cells after four-hour exposure of $2 \times 10^5$ cells/ml in serum-free medium for the diethyl ester as opposed to the dicarboxylic acid form. Four model compounds were used to demonstrate this feature. These four compounds are as follows:

1) γ-glutamyl-S(octyl)-cysteinyl-glycine, abbreviated "octyl G", has an $IC_{50}$ of >200 μM when in the dicarboxylic acid form; the $IC_{50}$ is 22 μM for the diethyl ester;

2) γ-glutamyl-S(hexyl)cysteinyl-R(-)-phenyl glycine, abbreviated "hexyl PG", has an $IC_{50}$ of >200 μM in its dicarboxylic acid form, but as the diethyl ester it has an $IC_{50}$ of 24 μM;

3) γ-glutamyl-S(benzyl)cysteinyl-R(-)-phenyl glycine, abbreviated "benzyl PG", also has an $IC_{50}$ of >200 μM in the free acid form, but an $IC_{50}$ of 47 μM for the diethyl ester;

4) γ-glutamyl-S(naphthyl)cysteinyl-glycine, abbreviated "naphthyl G", has an $IC_{50}$ of >200 μM but an $IC_{50}$ is 40 μM for the diethyl ester.

The foregoing values for $IC_{50}$ were determined as described above and the cells were assayed using the modified clonogenic assay described in Example 11 below.

In addition, both the esters and amides offer the opportunity to modify the invention compounds in ways that affect their suitability as therapeutic agents, as diagnostic reagents, and as ligands for coupling to solid supports. The ester or amide groups may contain additional useful ligands such as hydrophobic moieties to enhance cell permeation, reactive groups to facilitate linkage to other substances, and additional ligands such as antibodies or fragments thereof, carriers to enhance immunogenicity and the like. Further, the compounds can be modified by including substituents such as chelating agents which facilitate purification by immobilized metal ion affinity chromatography or substituents which alter the solubility of the peptide or which affect pharmacokinetics such as the addition of polyethylene glycol.

Thus, the esters, amides and hybrids of the compound of formula 1 offer distinct advantages over the free acid or salt forms in a variety of contexts.

The cycloamido forms of the compound of formula 1 offer the advantage of enhanced specificity and selectivity among target GSTs. The cyclic forms in general are superior as chromatographic ligands to the open chain forms. In addition, their inhibition characteristics are modulated by this feature.

The compounds of the invention that contain substituted benzyl as the embodiment of X are advantageous in that they offer the opportunity systematically to control the selectivity of the compounds for the various GSTs. For instance, as shown in Example 8 herein, the binding specificity among the μ and π groups of human GSTs is controlled by the nature of the para-substituent on a benzyl moiety attached to the sulfur atom of the Cys residue of certain compounds of the invention. There is a correlation in binding specificity with sigma (meta) values of the para-substituents on S-benzyl Cys moieties.

The four preferred compounds set forth above show clear selectivity with respect to GST isozymes. None of these compounds showed any appreciable inhibition of either glutathione reductase (where GSSG reduction was measured by the disappearance of NADPH) or of γ-glutamyl transpeptidase (where the transfer of glutamyl from glutamyl p-nitroanaline to glycylglycine was assessed). In these tests, all four compounds (as well as ethacrynic acid) had $IC_{50}$s of more than 1 mM. However, substantial differences were found with respect to the ability of each of these four compounds to inhibit GST isoenzymes. When the GST isoenzymes P1—1, A1—1, M1a—1a, and M2—2 were tested with respect to these compounds, the differences in selectivity became apparent. Benzyl PG and hexyl PG selectively inhibited P1—1 as compared to the remaining three isoenzymes, although hexyl PG showed reasonable inhibition with respect to A1—1. Thus, while benzyl PG showed Ki with respect to P1—1 of only 0.4 μM, the corresponding Ki values for the remaining A1—1, M1a—1a, and M2—2 were 20, 25 and 31 μM respectively. While hexyl PG measured a Ki of 0.85 μM with respect to P1—1, for the remaining enzymes, in order, the Ki values were 5.8, 41, and 97 respectively.

On the other hand, naphthyl G showed a Ki with respect to M1a—1a of only 0.1 μM; the values for P1—1, A1—1 and M2—2 were 1.2, 4.2 and 1.5 μM respectively. Octyl G was clearly selective for A1—1 giving a Ki value of 0.27 μM in comparison with 1.2 μM for M1a—1a and 1.9 μM for P1—1. The Ki values for ethacrynic acid with respect to all three isoenzymes are comparable: 4.0 μM for P1—1; 2.0 μM for A1—1 and 3.0 μM for M1a—1a.

Thus, benzyl PG and hexyl PG are particularly effective inhibitors for P1—1 to the exclusion of the other isoenzymes tested; naphthyl G is selective for M1a—1a and octyl G is selective for A1—1.

It is thus apparent that among the various compounds of the invention, analogs can be found that are selective for desired target GSTs. As is reflected in the examples below, this results in the ability to design therapeutic protocols according to the nature of the chemotherapeutic agent and its related detoxification mechanism and according to the GST complement of the targeted cells.

Use as Chromatographic Ligands and Analytical Reagents

The invention compounds also are useful individually as diagnostic chromatographic supports and chromatographic tools. The use of these compounds in affinity chromatography, for characterization and for purification, as well as in diagnostic assays, is particularly important in the case of human GSTs. While panels of the invention compounds are most convenient in determining the GST complement of tissues, individual compounds can be used to detect the presence of GSTs in general, or of GSTs of a particular type in humans, as well as in purification of particular types of human GSTs. Thus, as shown in Example 8 below, various compounds of the invention have different propensities for binding human GSTs of the μ (M1) and π (P1) classes, as well as various rat isoenzymes. In addition, as shown in Example 9, compounds of the invention also show selective solution phase inhibition of particular human GSTs. In most cases affinity chromatography and inhibition studies show the same enzyme specificity for each compound of the invention.

The compounds of the invention, or the compounds of formula 1 alone as the free acids or salts, can be used as chromatographic ligands for purification and characterization of human GSTs collectively, for purification and identification of human classes of GSTs or for purification or separation of individual human GST enzymes, depending on the choice of ligand.

For use as affinity ligands on chromatographic support, the compounds that include formula 1 are coupled to a suitable solid matrix, such as Sepharose, polyacrylamide, silica, and the like using standard coupling techniques. The noncyclic forms of the compounds of the invention contain at least amino and carboxyl functional groups which can be derivatized to suitable linkers or directly to supports. Depending on the nature of the solid support, the coupling of the affinity ligand may employ direct covalent coupling or may require the use of homo- or heterobifunctional linkers such as those available from Pierce Chemical Company (Rockford, Ill.). It may also be desirable to distance the affinity ligand from the surface of the support in order to render it more accessible. Such distancing can be accomplished using spacer arms, as is generally understood. Further, the support may be treated with an inert material, such as, for example, human serum albumin, so as to minimize unwanted interactions, especially if the support is to be used for the chromatography of biological samples.

The derivatized chromatographic supports may take advantage of the diversity of the compounds which include the structure of formula 1 by coupling the solid support to more than one such ligand. The ligands can be arranged in a gradient, at random as a mixture, or in any predetermined pattern desired. In addition, combinations of the compounds of the invention can be used in chromatographic applications wherein a balance is achieved between one or more compounds which serve as affinity ligands and one or more compounds which are used as competitors to the affinity ligand to effect elution of the materials subjected to chromatographic separation or characterization. Materials of varying affinity for the moieties subjected to the chromatographic technique are used for the ligands and the eluting agents, as illustrated in Example 10, below.

The chromatographic supports derivatized to compounds that include formula 1 may then be used for preparative separation of human GSTs or other enzymes for which the ligands have affinity, other enzymes utilizing glutathione as substrate, antibodies which react with glutathione, or other moieties which bind with moderate affinity to the ligands. Chromatographic supports coupled to the compounds of the invention may also be used in diagnosis to determine the presence, absence, quantity or nature of materials in biological or other samples suspected to contain materials having similarity in structure to glutathione. For instance, affinity chromatography using compounds of the invention in a novel HPLC method can be used to isolate and separate GST isozymes in dimeric, bioactive form from human tissues such as liver, as illustrated in Example 10, below.

The suitable compound containing the structure of formula 1 useful in such separations or analyses may be evident from the nature of the analyte or material whose preparation is desired, or may readily be determined by preparing a diverse panel of the compounds and screening the panel for the most effective affinity ligand.

The compounds containing the structure of formula 1 may also be used for detecting the presence or absence of human GSTs in general or for a particular class or isoenzyme thereof. Protocols for such assays mimic those used in immunoassay; these protocols are generally applicable to any assays which involve specific binding partners where the specificity of the assay depends on the specificity of the binding. Thus, in such assays, the compounds including the structure of formula 1 play the role of antibodies or other immunoreactive agents specific for the analyte, in this case the relevant GST. Such protocols include sandwich assays, competition assays, direct binding assays and the like with a wide variety of detection means for formation of "immunocomplexes" (in this case a complex between GST and the compound containing the structure of formula 1). Such detection means include florescent tags, enzyme labels, radioactive labels and combinations of these.

Synthesis of the Tripeptide Analogs

The tripeptide analogs of the invention or additional tripeptide analog members of diverse panels can be synthesized using means generally known in the art, but using modifications which render these general methods applicable to the desired tripeptide. Although solid-phase synthesis methodologies can be used, liquid-phase peptide synthesis appears superior for these short peptides. The Fmoc reagents originally developed for solid-phase synthesis can be applied to a solution-phase method for producing 100 mg quantities of the tripeptide analogs.

The intermediate protected dipeptides and tripeptides synthesized using solution-phase Fmoc chemistry are isolated by chromatography on silica gel, and deprotected in mild base, thus allowing synthesis of acid-labile thioconjugates (Iselin, B., et al., *Helv Chem Acta* (1955) 38:1508–1516). The analogs can be purified and recovered, or the crude product mixtures may be directly coupled to solid support to provide affinity-derivatized supports (Sundburg, L., et al., *J Chromatog* (1974) 90:87–98).

In those circumstances where ester of the C-terminal amino acid $AA_C$ is not available, the ester is made by synthesizing the N-Fmoc-protected amino acid (Atherton, E., et al., in "Solid Phase Peptide Synthesis," IRL Press, Oxford, England (1989), pages 47–61) and then esterified by treatment with the desired alcohol in the presence of concentrated sulfuric acid (Benoiton, L., *Can J Chem* (1962) 40:570–572). Nonesterified materials are removed by extractions with mild base and the desired N-Fmoc amino acid ester is isolated by evaporation.

The sulfur-functionalized Fmoc cysteine derivatives are made in a one-pot procedure by treating cysteine with Fmoc-OSu as pH 9 and then treating this mixture with the appropriate alkylating agent.

The synthesis is conducted as shown in Reaction Scheme 1.

Reaction Scheme I

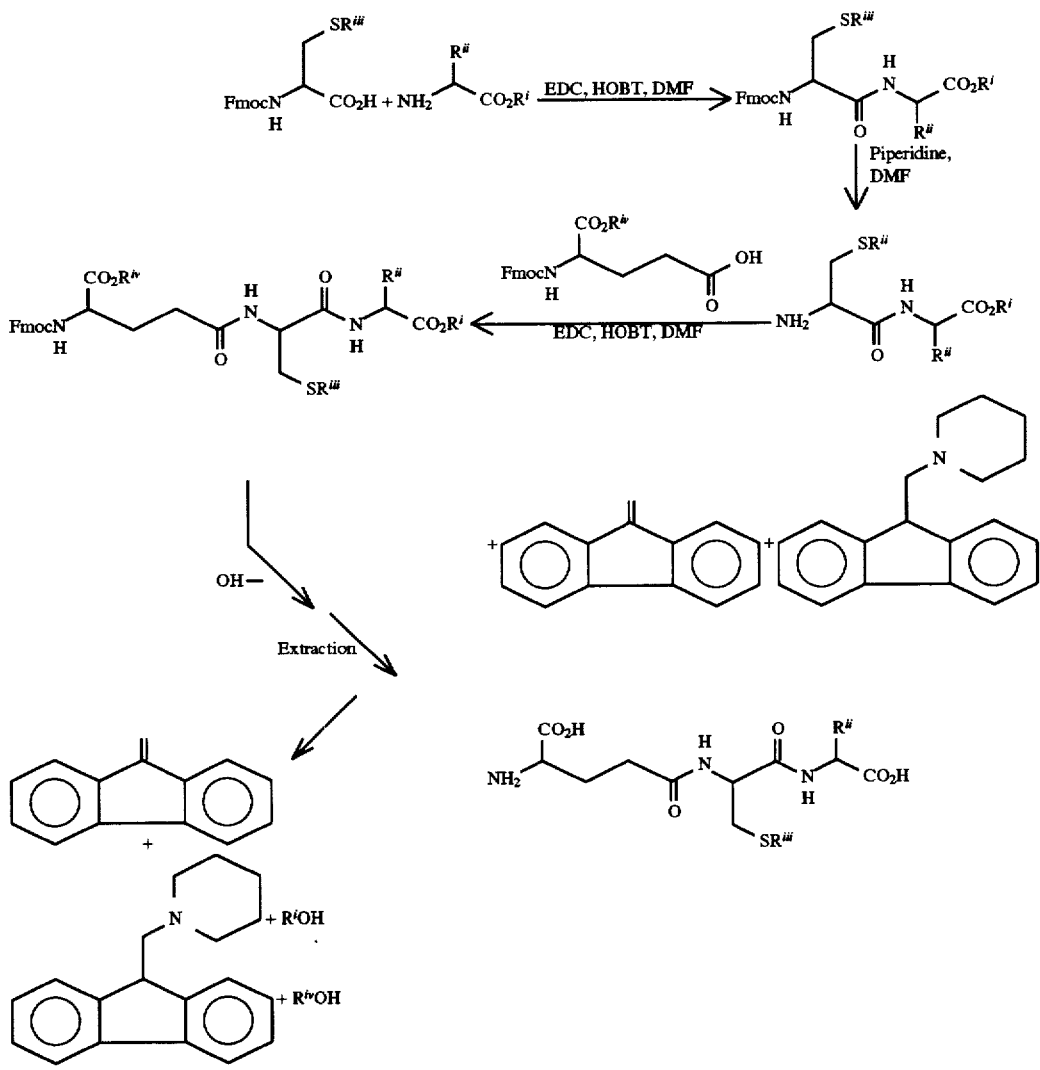

Coupling the cysteine derivative to the C-terminal amino acid is accomplished with the water-soluble carbodiimide EDC (Sheehan, J., et al., *J Org Chem* (1961) 26:2525–2528) and HOBT (Konig, W., et al., *Chem Ber* (1970) 103:788–798) (added to retard undesired racemization and speed up the reaction) in DMF. After coupling is complete, usually about 1 hr at r.t., the mixture is reduced in vacuo and poured into $KHCO_3$ solution (John Hughes, private communication). This step extracts most of the DMF and EDC and EDC urea, as well as some of the Fmoc-cysteine derivative which did not couple. The resulting gummy residue is retained by decanting off the liquid. This crude dipeptide is dissolved in EtOAc and washed with 1N hydrochloric acid and water to remove any remaining uncoupled C-terminal amino acid ester, as well as residual EDC and EDC urea. The solution is concentrated and the dipeptide purified by chromatography.

The recovered dipeptide is then treated with 25% piperidine in DMF for 30 min to remove the Fmoc group. The dibenzofulvene or its piperidine adduct resulting from Fmoc removal should not affect the results of the next coupling (Atherton, E., et al., *J Chem Soc Perkin Trans* (1981) 1:538–546). Any excess piperidine, however, must be removed, which is accomplished by repeated co-evaporation with DMF until the odor of piperidine is no longer detectable in the deblocked material. The second coupling is then performed with the glutamic acid derivative followed by the same workup as for the dipeptide.

Fmoc glutamic acid α-benzyl ester is made in good yield and purity from commercially available glutamic acid a-benzyl ester. Fmoc-glutamic acid α-tert butyl ester, also commercially available, can also be used, but this requires a separate acid treatment step in the workup. There are solubility problems with some of the protected tripeptides during this step, and impure, partially deprotected products are often obtained.

The material produced by the coupling of the glutamic acid derivative to the dipeptide and workup contains several chromatographically mobile components. The material that elutes first from the final column is fluorescent, suggesting dibenzofulvene. The putative desired product elutes next along with another UV-absorbing material, which is probably the piperidine adduct of dibenzofulvene. Since similar products are generated and separated from the deblocked tripeptide during the final workup, these contaminants are not removed at this stage.

Once the protected tripeptide (and impurities) are isolated, it is dried under vacuum and treated with 0.25N NaOH in 3:1 ethanol:water for 18 hrs. This removes the Fmoc and ester-protecting groups. When t-butyl-protected glutamic acid is used, 3N HCl in ethanol/water 3/1 v/v for 3 hr is used to remove the t-butyl group before the base treatment. The acid is removed by rotary evaporation and co-evaporation with ethanol and water, and the same base treatment as above removes the remaining protecting groups. After the overnight base treatment, addition of water and extraction with hexane removes the organic by-products of the deprotection. The aqueous solution of the peptide is acidified and reduced to a solid. Dissolution of the peptide in ethanol and filtration removes the salt. This is evaporated to a foam and subjected to high vacuum overnight.

The compounds are analyzed by HPLC, TLC and FAB mass spectroscopy. While the TLC analysis show good results in most cases, the HPLC results are mixed, partially because the analysis conditions used were not optimized for some of the more hydrophobic (S-alkyl C-terminal valine, β-alanine and 4ABu) peptides.

Racemization during the final deprotection with base may occur in some small amount, particularly with the phenylglycine analog (Bodansky, M., et al., in "Practical Methods in Peptide Synthesis," Springer Verlag, Berlin (1984)). This is less than that which occurs with the sodium-ammonia conditions used previously by Adang, A. et al. (*Biochem J* (1989) 264:721–724).

Using the techniques set forth above, the analogs of Table 1 were prepared.

TABLE 1

| Compound[a] | Yield, %[b] | TLC $R_f$[c] | M/e[d] | Loading[e] |
|---|---|---|---|---|
| γE-C(Bz)-G | 32 | 0.49 | 388.2, 402.2[f] | 1.0 |
| γE-C(Pr)-A | 23 | 0.71 | 365.2 | 9.0 |
| γE-C(Hx)-A | 17 | 0.76 | 406.2, 428.2[f] | 4.8 |
| γE-C(Bz)-A | 44 | 0.35 | 412.2, 434.2[f] | 6.6 |
| γE-C(Trt)-A | 15 | 0.83 | 586.4[f] | 1.2 |
| γE-C(Me)-βA | 27 | 0.58 | 357.1[f] | |
| γE-C(Pr)-βA | 27 | 0.41 | 364.1, 386.1[f] | |
| γE-C(Hx)-βA | 13 | 0.49 | 406.3, 428.3[f] | 6.0 |
| γE-C(Bz)-βA | 17 | 0.66 | 434.2[f] | 8.1 |
| γE-C(Trt)-βA | 42 | 0.92 | 564.3, 586.5[f] | N/A |
| γE-C(Pr)-4ABu | 13 | 0.51 | 378, 400[f] | |
| γE-C(Hx)-4ABu | 17 | 0.52 | 402.3, 424.3[g] | 4.6 |
| γE-C(Bz)-4ABu | 23 | 0.70 | 426, 448.2[f] | 4.0 |
| γE-C(Pr)-V | 23 | 0.67 | 391 | 13.7 |
| γE-C(Hx)-V | 15 | 0.64 | 434.2, 456.2[f] | 19.5 |
| γE-C(Bz)-V | 26 | 0.73 | 440.1, 462.1[f] | 6.5 |
| γE-C(Pr)-D | 33 | 0.55 | 408 | 7.0 |
| γE-C(Hx)-D | 25 | 0.68 | 451.2 | 5.9 |
| γE-C(Bz)-D | 22 | 0.59 | 456.1, 478.1[f] | 2.4 |
| γE-C(Pr)-PG | 14 | 0.64 | 426.4, 448[f] | |
| γE-C(Hx)-PG | 13 | 0.63 | 468.3 | 4.8 |
| γE-C(Bz)-PG | 11 | 0.61 | 474.1, 496.1[f] | 2.0 |
| γE-C(Pr)-H | 6 | 0.57 | 429.2 | |
| γE-C(Hx)-H | 30 | 0.61 | 473.3 | 6.0 |
| γE-C(Bz)-H | 11 | 0.58 | 499.3[f] | 1.0 |

[a]Standard one-letter AA code, with Me = methyl, Pr = n-propyl, Hx = n-hexyl, Bz = benzyl, Trt = trityl (triphenyl methyl).
[b]Moles of deprotected product divided by the moles of Fmoc-cysteine derivative used.
[c]TLC $R_f$ values for silica plates eluted with EtOAc/pyridine/HOAc/water 5/5/3/1 and visualized with ninhydrin spray.
[d]Observed molecular mass, in AMU, usually the molecular weight plus 1. Thioglycerol or nitrobenzyl alcohol matrix.
[e]Micromoles of peptide per ml of swollen resin volume (water)
[f]Sodium adduct, M + 22.
[g]Molecular ion and sodium adduct minus water; MH[+] − 18.

In addition, other compounds of formula 1, including the cycloamido forms of these compounds, as well as the ethyl and benzyl esters thereof, are prepared.

The following examples are intended to illustrate, but not to limit, the invention.

EXAMPLE 1

Synthesis of 9-Fluorenylmethoxycarbonyl-4-aminobutyric acid ethyl ester

Forty-five g (0.1339M, 0.94 eq) of Fmoc-Osu was added slowly to a solution of 14.75 g (0.143M, 1 eq) of 4-aminobutyric acid (4-ABu) and 20 g of $Na_2CO_3$ in 300 ml of deionized water and 200 ml of tetrahydrofuran (THF). The pH was monitored and more $Na_2CO_3$ was added to keep the pH above 8. The reaction was stirred for 2 hr and then acidified with conc. HCl. The resulting cloudy suspension was extracted with 600 ml of ethyl acetate (EtOAc), after which the organic layer was further extracted with 300 ml 0.5N NaOH. The aqueous layer was rapidly poured into 20 ml of conc. HCl in 500 ml of ice water. The resulting white suspension was extracted with 300 ml of EtOAc, dried over 50 g of $Na_2SO_4$ and evaporated to 35 g (76% yield) of Fmoc-4-ABu as a white powder. This was dissolved in 500 ml of absolute ethanol and 40 ml of conc. $H_2SO_4$ was added. After 4 hrs, the solution had become a semi-solid white mass. This was poured into 2 L of water and filtered. The white material was dissolved in 500 ml of EtOAc and extracted once with 200 ml of 0.5N NaOH, dried and evaporated to give 30 g (79% yield) of total compound, $R_f$ 0.71 (20% MeOH in $CH_2C_2$), mp 83°–86°. Anal. Calcd. for $C_{21}H_{23}NO_4$: C, 71.37; H, 6.56; N, 3.96. Found: C, 71.42; H, 6.67; N, 3.72.

EXAMPLE 2

Synthesis of 9-flourenylmethoxycarbonyl-phenylglycine ethyl ester

In a similar synthetic procedure, 20 g of phenylglycine gave 33.7 g (68% yield) of Fmoc-phenylglycine. 19 g of this product was converted into 10 g (57% yield) of product, $R_f$ 0.95 (same TLC system), mp 130°–133°. Anal. calcd. for $C_{25}H_{23}NO_4$: C, 74.80, H, 5.77, N, 3.49. Found: C, 74.72, H, 5.91, N, 3.20.

EXAMPLE 3

Synthesis of 9-fluorenylmethoxycarbonyl-aspartic acid dimethyl ester

Forty-five g (0.134M, 0.96 eq) of Fmoc-Osu was added to 20 g (0.15M, 1 eq) of aspartic acid and 20 g of $Na_2CO_3$ dissolved in 400 ml of water and 200 ml of dioxane. The mixture was stirred for 2 hrs while the pH was maintained at about 9 by the addition of small amounts of $Na_2CO_3$. Then the cloudy white mixture was poured into 500 ml of ice water containing 40 ml of conc HCl. The white solid was extracted with 500 ml EtOAc and this was mixed with 500 ml of hexane. The mixture was chilled overnight and stirred the next day to give 38 g of Fmoc-aspartic acid as crystals (71% yield) upon filtration and air drying. 10 g (0.28M) of this product was dissolved in 200 ml of methanol and 20 ml of conc $H_2SO_4$ was added. The solution was allowed to stand overnight. The mixture was poured into 1 L of water and filtered. The resulting white solid was dried and redissolved in EtOAc. Slow addition of hexane and chilling gave 9 g (83% yield) of product as white needles, mp 78°–80°. $[\alpha]_d = -13.9°$. Anal. calcd. for $C_{21}H_{21}NO_4$: C, 65.78, H, 5.52, N, 3.65. Found: C, 66.18, H, 5.68, N, 3.69.

EXAMPLE 4

Synthesis of 9-flourenylmethoxycarbonyl-S-hexyl cysteine

A. Twenty g (0.127M, 1 eq) of cysteine hydrochloride and 20 g $Na_2CO_3$ was dissolved in 800 ml of water under a stream of argon. Two hundred ml of $CH_3CN$ was added, and then 42 g (0.122M, 0.96 eq) of Fmoc-Osu was added in small portions while the pH was maintained at about 9 by adding 5 g portions of $Na_2CO_3$. The reaction was stirred for an additional 2 hrs, and 18.6 ml (26.8 g, 0.126M, 0.99 eq) of 1-iodohexane was added as a solution in 200 ml of $CH_3CN$. The reaction was stirred for an additional 2 hrs and poured into 1 L of ice water and 50 ml of conc HCl. The white mixture was extracted with 600 ml of EtOAc, and the organic layer was extracted with 2 500 ml portions of 1N KOH. Each of these was immediately dropped into separate portions of 500 ml of water and 30 ml of conc HCL, and the cloudy mixtures obtained were each extracted with 500 ml of EtOAc. These were each dried over $Na_2SO_4$ and evaporated. The total yield was 24.6 g (45%). The second fraction (3.5 g) crystallized on standing, mp 101°–103°. $R_f$=0.57. $[a]_d$=−14.3°. Anal. Calcd. for $C_{21}H_{23}NO_4S$: C, 65.42. H, 6.01. N, 3.63. Found: C, 65.53. H, 5.74. N, 2.91.

B. Additional S-functionalized Fmoc cysteine derivatives were prepared as set forth in paragraph A.

EXAMPLE 5

Synthesis of Fmoc-glutamic acid α-benzyl ester

Twenty-five g (0.105M) glutamic acid α-benzyl ester and 25 g $Na_2CO_4$ was dissolved in 400 ml of water and 200 ml THF was added. 34 g (0.101M, 0.96 eq) Fmoc-OSu was added in small portions with stirring, and the pH was kept at about 9 by adding more $Na_2CO_3$ as needed. After 1 hr, the reaction was poured into 500 ml of water and acidified with conc HCl. The white suspension was extracted with EtOAc, dried over $Na_2SO_4$ and evaporated to a solid mass. This was dissolved in 500 ml hot EtOAc and 300 ml hexane was added. Overnight chilling, collection and air-drying gave 38.7 g (83% yield) of white crystals, mp 110°–112°. $[a]_d$= −13.8°. M/e (Rel. inten.): 460.2 (19), 363.4 (8), 345.4 (19), 307.2 (10), 289.2 (12), 238.2 (12), 191.2 (10), 178.2 (89), 165.1 (23), 154.1 (57), 136.1 (48). $^1$H NMR (400 mHz), PPM: 1.9 (m, 1H), 2.2 (m, 1H), 2.4 (M, 2H), 4.1 (t, 1H), 4.4 (d, 2H), 4.43 (m, 1H), 5.1 (s, 2H), 5.6 (d, 1H), 7.3 (m, 9H), 7.5 (d, 2H), 7.7 (d, 2H), 9.4–9.6 (broad s, 1H). $^{13}$C (100 mHz), PPM: 27.5, 30.0, 47.3, 53.5, 67.3, 67.7, 120.2, 125.0, 127.3, 128.5, 128.8, 129.2, 135.2, 141.5, 143.6, 143.9, 156.3, 171.4, 177.8. Anal. Calcd. for $C_{27}H_{25}NO_6$: C, 70.57. H, 5.48. N, 3.05. Found: C, 69.71. H, 5.58. N, 2.88.

EXAMPLE 6

Synthesis of γ-glutamyl S-benzyl cysteinyl β-alanine 1.5 g (9.76 mmol, 1 eq) of β-alanine ethyl ester hydrochloride was added to 50 ml of DMF and 1.8 ml of DIPEA was added. 3.5 g (8.1 mM, 0.83 eq) of Fmoc-S-benzyl cysteine was added and dissolved by swirling the solution. Next 2 g of EDAC and 250 mg of HOBT were added, and the solids were dissolved by swirling. The mixture was allowed to stand for 1 hr, and was concentrated in vacuo to a mobile oil of about 5 ml in volume. To this was added 100 ml of 10% weight/volume $KHCO_3$ in water, and the mixture was shaken and the liquid removed by filtration. The residue was dissolved in 100 ml of EtOAc, washed with 50 ml of 1N HCl, 50 ml of water and dried over $Na_2SO_4$. The solution was filtered and concentrated in vacuo to give a foam which was chromatographed using a 2×6 cm bed of silica gel packed in $CH_2Cl_2$. The column was eluted until the first UV absorbing material appeared, then a gradient was run in 1% methanol increments of 100 ml volume to 3%. methanol. A strong UV absorbing band eluted after two portions of 3% methanol; these were checked for purity by TLC and pooled and evaporated in vacuo to give 4.6 g (83% yield) of Fmoc-Cys(S-benzyl)-β-alanine ethyl ester. Half of this (4 mmol) was dissolved in a mixture of 30 ml DMF and 10 ml piperidine, and allowed to stand for 30 min. The solution was reduced to a solid in vacuo, and the process was repeated twice again with 50 ml of DMF. The resulting white solid was subjected to a high vacuum for 1 hr, then it was dissolved in 50 ml of DMF. For the second coupling step, 1.6 g (3.5 mmol, 0.9 eq) of Fmoc-glutamic acid (α) benzyl ester (v) was added, followed by 0.8 g (4.2 mmol, 1.05 eq) of EDAC and 200 mg (1.4 mmol) of HOBT. The mixture was allowed to stand 1 hr, and concentrated in vacuo to about 5 ml in volume. This was poured into 100 ml of 10% aqueous $KHCO_3$ solution and shaken. The liquid was poured off, and the residue was dissolved in 100 ml of ethyl acetate. The organic layer was washed with 50 ml of 1N HCl, 50 ml of water, and dried over $Na_2SO_4$. This was reduced to a tar and chromatographed in the same manner as the protected dipeptide. 1.2 g (42% yield) of the protected tripeptide was obtained. This material was dissolved in 30 ml of absolute ethanol and 10 ml of 1N NaOH solution was added. The mixture was allowed to stand for 18 hrs, and was poured into a separatory funnel with 40 ml of water and 40 ml of hexane. The layers were shaken and separated, and the aqueous phase was washed with an additional 40 ml of hexane. The pH of the water layer was adjusted to about 3 by adding a few drops of conc HCl, and the cloudy solution was reduced to a solid in vacuo and subjected to a high vacuum for several hrs. The residue was washed with 2 20 ml portions of absolute ethanol. The ethanol-NaCl slurry was filtered, and the clear solution was evaporated to a tar. The weight was 620 mg (89w yield from the protected tripeptide, 19% from Fmoc-Cys(Benzyl)—OH). A TLC plate was run in ethyl acetate/pyridine/water/acetic acid 5/5/3/1 v/v and visualized with ninhydrin spray and heat (Stewart, J. et al., "Solid Phase Peptide Synthesis" (1984) pp. 53–124, Pierce Chemical Co., Rockford, Ill., $R_f$ 0.66. HPLC analysis showed 74% purity by area integration of UV absorbing material (FIG. 1). Fast atom bombardment Mass spectroscopy (FABMS) showed an ion peak at 434.2 M/e, consistent with the tripeptide monosodium salt. Other higher mass peaks were also present, attributable in part to incompletely deprotected peptide.

In cases where the Fmoc protected C-terminal amino acid ester was used instead of the commercially available free amino C-terminal amino acid ester, this material was deblocked with the same procedures as those used to deblock the protected dipeptide above, then proceeding with the first coupling reaction as above.

EXAMPLE 7

Derivatization to Sepharose Resin 0.66 g epoxy Sepharose™ 6B (Pharmacia) was swollen with 10 ml water for 15 min, then rinsed twice with 10 ml water in a 15 ml sintered glass funnel. A solution of 100–500 mg of the crude tripeptide in 5 ml ethanol and 10 ml water was adjusted to pH 11–12 with 6N NaOH in a 20 ml scintillation vial with a polycone cap. The rinsed resin was added, and gently agitated overnight in a 37° water bath. The pH was checked the next day and brought back to pH 11–12 with 6N NaOH if needed. After another day of agitation, the resin was filtered (the peptide-containing liquid was acidified with conc HCl, evaporated and saved) and rinsed three times with 10 ml water. The unfunctionalized epoxy groups were capped by soaking the resin in 10 ml of water which contained about 0.1 ml ethanolamine for 1 hr. The resin was then rinsed three times with 10 ml water, and a sample was removed for analysis. The remainder was rinsed with 10 ml of 0.1M NaOAc, 0.5M NaCl pH 4.0 buffer, followed by 10 ml of 0.1M tris chloride, 0.5M NaCl pH 8.0 buffer. The resin was stored at 4° C. in this pH 8 buffer.

EXAMPLE 8

Use of the Compounds of the Invention as Affinity Sorbents

A series of the compounds of formula 1 was constructed wherein YCO was γ-Glu, AA$_C$ was Gly, and X was benzyl having at the para position, nitro, chloro, methoxy and methyl substituents. The relevant analogs were derivatized to Sepharose resin as described above and used as affinity sorbents in the separation of three recombinant human GST enzymes. HPLC was used to measure the relative amounts of the enzymes which bound to the supports.

The results are shown in Table 2.

TABLE 2

| Substituent | % π | % μ |
| --- | --- | --- |
| NO$_2$ | 95 | 5 |
| Cl | 89 | 11 |
| OMe | 70 | 17 |
| Me | 3 | 94 |

When the percentage of π and μ isoenzymes were plotted against their sigma (meta) values good linear correlation was obtained. However, poor correlation was obtained when the sigma (para) values were used. The sigma (meta) values are a measure of purely inductive effect; however, the sigma (para) values are dependent on resonance in which the substituent can place partial charges at an atom in the ring next to the point of attachment.

The recoveries of protein and GST (CDNB-conjugating) activity in the elution fractions after affinity purification of rat liver cytosolic GST isoenzymes on various compounds of the invention are shown in Table 3.

TABLE 3

Recovery of protein and CDNB-conjugating activity after affinity chromatography of rat liver cytosol on GSH and selected GSH analog sorbents

| Sorbent | Protein (μg) | Protein (% total) | Activity (μmol/min/ml) | Activity (% total) |
| --- | --- | --- | --- | --- |
| HxGSH | 60 | 3.0 | 1.32 | 67 |
| S-L-GSH | 51 | 2.5 | 1.21 | 61 |
| γE-C(Cu)-G | 49 | 2.5 | 0.64 | 32 |
| γE-C(Bz)βA | 20 | 1.0 | 0.69 | 35 |
| γE-C(Bz)-A | 11 | 0.5 | 0.43 | 22 |
| γE-C(Hx)-φG | 4 | 0.2 | 0.10 | 5 |

Abbreviation: Cu = cumyl (α,α-dimethylbenzyl)

Traditional S-L-GSH and HxGSH sorbents showed high binding and broad isoenzyme recognition. The novel sorbents retained a lower mass of the GST isoenzymes, with the protein recovery for three of the novel sorbents being less than half that of the traditional sorbents.

In comparison with HxGSH, the novel sorbents did not show a direct correspondence of CDNB-conjugating activity with protein recovery. For example, γE-C(Bz)-βA and γE-C(Bz)-A sorbents gave 33% and 16% of the protein recovery seen with HxGSH, but the CDNB-conjugating activities were far higher (52% and 33% respectively) after correcting for the inhibitory properties of the eluting ligand. In contrast, protein recovery by γE-C(Cu)-G sorbent decreased minimally, while activity decreased by 50%. It is well known that different GST isoenzymes display individual specific activities with CDNB. The discrepancy between protein recovery and activity recovery was attributed to differences in the isoenzyme composition in the elution fractions of each sorbent. This hypothesis was supported by SDS/PAGE and reverse-phase HPLC analysis of the eluate fractions.

Fractions eluted from the sorbents listed in Table 3 were analyzed by SDS/PAGE followed by silver staining. S-L-GSH and HxGSH sorbents bound proteins which corresponded to the previously observed electrophoretic band pattern of rat liver GST subunits. The novel sorbents displayed different band patterns. For example, the γE-C(Bz)-βA eluate referred to above showed a highly enriched band for presumptive μ-class isoenzymes. As the π-class GST 7-7 is found at low levels in rat liver cytosol, other rat tissues known to express higher levels of this isoenzyme also were tested. The GST gel pattern from rat kidney cytosolic proteins eluted from the γE-C(Hx)-φG sorbent showed a protein with the same molecular migration as rat GST subunit 7 is the unique component of this eluate, indicating that this sorbent is a π-selective reagent.

A protein with a molecular migration similar to that of another GSH-dependent enzyme, glyoxalase I, was also present in the eluates from γE-C(Bz)-A and γE-C(Bz)-βA, but was not detected in eluates from the other sorbents. In these experiments HxGSH, previously shown to bind glyoxalase I, did not show any detectable levels of this GSH-dependent enzyme. Glyoxalase I is known to be a metal-dependent enzyme, and the presence of EDTA in the buffers may have interfered with binding activity.

The high degree of purity of appropriately sized proteins seen by SDS/PAGE of the affinity-eluted proteins suggested that the observed bands are indeed GSTs. Independent confirmation of this conclusion, at higher resolution, was provided by reverse-phase HPLC analyses of the GST isoenzymes in the eluates from different sorbents. Comparison with purified GST standards showed that the isoenzymes eluted from the novel sorbents correspond to known GST isoenzymes. These procedures showed that GST subunit 3 eluted at 14 min, subunit 4 at 17 min, subunit 7 at 18 min, subunit 2 at 23 min, subunit 6 at 25 min, subunits 1a and 1b at 37 and 40 min, and subunit 8 at 42 min. Subunits 3, 4 and 6 are μ-class isoenzymes, subunits 1a, 1b, 2 and 8 are α-class isoenzymes, and subunit 7 is the π-class isoenzyme. S-L-GSH and HXGSH sorbents, as expected, bound all except 5—5, the Theta-class isoenzyme.

γE-C(Cu)-G increased the proportion of isoenzyme 2, yet bound all the isoenzymes to some extent. In contrast, other sorbents were very selective in their binding of the isoenzymes. For example, γE-C(Bz)-βA selectively bound the μ-class isoenzymes 3 and 4, confirming the SDS/PAGE results.

The specificities of a variety of the novel sorbents for rat cytosolic GST isoenzymes are summarized in Table 4. Some structural alterations of the ligand produced sorbents that did not effectively bind any isoenzyme; several of these are listed for completeness.

TABLE 4

Separation of rat GST isoenzymes by novel sorbents

| Sorbent* | Isoenzyme subunit specificity | Protein recovery (%) |
|---|---|---|
| High binding, nonselective | | |
| Hx-GSH | All | 3.0 |
| S-L-GSH | All | 2.5 |
| Selective | | |
| γE-C(Cu)-G | 2 > 3 > 4 | 2.5 |
| γE-C(BuBz)-G | 2 > 4 > 3 > 7 | 1.7 |
| γE-C(Bz)-A | 4 > 3 >> 6 > 2 | 0.5 |
| γE-C(Bz)-βA | 3 = 4 >> 2 > 6 | 1.0 |
| γE-C(Pr)-H | 4 > 3 >> 2 | 1.0 |
| γE-C(Pr)-A | 3 = 4 > 2 > 1 > 6 > 7 | 1.4 |
| γE-C(Hx)-φG | 7 >> 3 = 4 | 0.2 |
| γE-C(Bz)-φG | 7 >> 2 = 3 = 4 | 1.3 |
| Weak binding | | |
| γE-C(Pr)-V | Little: 2 = 3 = 4 | 0.5 |
| γE-C(Hx)-V | Little: 2-3-4 | 0.4 |
| γE-C(Pr)-D | Little: 3 > 2 > 4 | 0.2 |
| γE-C(Hx)-D | None | 0.1 |
| γE-C(Bz)-H | None | 0.1 |

*Abbreviations as in Table 1 and text above, except Cu = cumyl (α, α-dimethylbenzyl) and φG = phenylglycine.

Systematic alterations of the Cys residue to probe the previously defined H-site (hydrophobic pocket) resulted in ligands capable of binding to the isoenzymes. Adang et al. (1990) did not examine any analogues with systematic modifications of groups attached to the Cys moiety. Alterations of this group had effects on the level of protein recovery and the specificity of isoenzyme binding in several cases. For instance, alteration of the S-linked moiety of glutathione to a structure similar to that of cumene hydroperoxide, an α-class substrate, made the sorbents preferential for isoenzyme 2—2 of the α-class. When Ala was used as the terminal amino acid, both propyl and benzyl moieties on the Cys resulted in sorbents specific for μ-class isoenzymes (Table 4). The propyl sorbent retained more GST protein, in part because it picks up both isoenzymes 3 and 4, compared with the benzyl sorbent, which is highly specific for isoenzyme 4. When His was used as the terminal amino acid, the propyl moiety resulted in high μ-class specificity, while the benzyl moiety resulted in no binding at all. In contrast to these sorbents, alterations of the Cys moiety of Val- and Asp-substituted sorbents had no effect on the low binding. Thus, the Cys substituent can be important in modifying the overall specificity of the sorbent as determined by the terminal amino acid.

EXAMPLE 9

Use of the Compounds of the Invention as Solution Phase Inhibitors

Screening Strategy

A systematically diversified set of peptide analogs of the invention has been tested as isozyme-specific inhibitors of human glutathione-S-transferase (GST). The potency of the best of the inhibitors is in the 0.5 to 20 micromolar range, with kinetics indicative of competitive inhibition with glutathione at the active site. The specificity observed among three recombinant-derived GST isozymes at both low and high potency ranged from negligible to high (at least 20-fold over the next most sensitive isozyme).

These compounds were initially screened at 1-mM concentrations against three recombinant human GSTs, one from each major isoenzyme class, to see if they would inhibit the enzyme activity, using CDNB as a spectrophotometrically detectable substrate. To permit the rapid testing of a wide spectrum of compounds, the paralogs used at this stage were crude synthetic samples and were not characterized for purity before testing, although in most cases the intended synthetic compound was the dominant species, representing about 50% of the mass. The nominal 1-mM concentration was based on an assumption of 100% purity. Table 5 shows the results of these inhibition tests for a series of 51 paralog analogs of GSH.

TABLE 5

Inhibition of human GST activity by GSH analogs

| | | % Inhibition at 1 mM | | | μM Conc. for IC$_{50}$ | | |
|---|---|---|---|---|---|---|---|
| No. | Structure | P1-1 | A1-1 | M1a-1a | P1-1 | A1-1 | M1a-1a |
| Peptide analogs of GSH showing inhibition bias toward P1-1: | | | | | | | |
| 1 | γE-C(Hx) (IMe)-φG | 99 | 96 | 83 | 35 | 36 | 450 |
| 2 | γE-C(p-ClBz)-φG | 99 | 92 | 89 | | | |
| 3 | γE-C(octyl)-φG | 96 | 92 | 90 | 100 | 1000 | 300 |
| 4 | γE-C(Bz)-φG | 85 | 68 | 30 | | | |
| 5 | γE-C(Hx)-R(-)φG | 75 | 62 | 4 | | | |
| 6 | γE-C(Hx)-S(+)φG | 71 | 61 | 48 | 4 | 12 | 100 |
| 7 | γE-C(decyl)-φG | 70 | 60 | 60 | 300 | 300 | 500 |
| 8 | γE-α-aminooctanoic-G | 52 | 1 | 8 | | | |
| Peptide analogs of GSH showing inhibition bias toward A1-1: | | | | | | | |
| 9 | γE-C(octyl)-G | 99 | 99 | 99 | 7 | 1 | 1 |
| 10 | γE-C(Hx)-G | 93 | 99 | 99 | 75 | 25 | 40 |
| 11 | γE-C(p-NO$_2$Bz)-φG | 90 | 99 | 99 | | | |
| 12 | γE-C(octyl) (IMe)-G | 90 | 99 | 99 | 50 | 20 | 50 |
| 13 | γE-C(Bz)-4ABu | 70 | 70 | 95 | 575 | 575 | 570 |
| 14 | G-γE-C(octyl)-G | 99 | 91 | 90 | 500 | 100 | 100 |
| 15 | cyclic γE-C(Hx)-φG | 53 | 85 | 80 | | | |
| 16 | γE-C(Bz)-4ABu | 4 | 78 | 44 | | | |
| 17 | γE-C(2,5-dichloroBz)-G | 50 | 70 | 90 | 1150 | 570 | 570 |
| 18 | γE-C(Bz)-V | 35 | 64 | 74 | | | |
| 19 | γE-C(Bz)-D | 12 | 62 | 57 | 900 | 900 | |

TABLE 5-continued

Inhibition of human GST activity by GSH analogs

| | | % Inhibition at 1 mM | | | μM Conc. for IC$_{50}$ | | |
|---|---|---|---|---|---|---|---|
| No. | Structure | P1-1 | A1-1 | M1a-1a | P1-1 | A1-1 | M1a-1a |
| 20 | γE-C(Hx)-4ABu | 25 | 58 | 83 | 3000 | 875 | 1750 |
| 21 | γE-C(Hx)-V | 24 | 48 | 47 | | | |
| 22 | γE-C(Hx)-D | 0 | 35 | 30 | 20000 | 2000 | 2000 |
| 23 | γE-C(Pr)-H | 2 | 17 | 3 | | | |
| 24 | γE-C(Hx)-H | 8 | 11 | 1 | | | |
| Peptide analogs of GSH showing inhibition bias toward M1a-1a: | | | | | | | |
| 25 | γE-C(p-ClBZ)-G | 85 | 98 | 99 | 200 | 20 | 9 |
| 26 | αE-C(Hx)-φG | 78 | 80 | 99 | | | |
| 27 | γE-C(p-MeBz)-G | 70 | 90 | 99 | 500 | 150 | 40 |
| 28 | γE-C(Hx)-βA | 8 | 69 | 99 | | | |
| 29 | γE-C(p-MeBz)-βA | 55 | 65 | 99 | 800 | 600 | 20 |
| 30 | γE-C(Bz)-βA | 0 | 25 | 99 | 1000 | 1000 | 25 |
| 31 | cyclic γE-C(Bz)-φG | 11 | 36 | 95 | 6000 | 1500 | 70 |
| 32 | γE-C(3,5-difluoroBz)-G | 70 | 70 | 95 | 575 | 575 | 570 |
| 33 | γE-C(Bu)-G | 91 | 865 | 93 | 48 | 106 | 21 |
| 34 | γE-C(Trt)-A | 46 | 30 | 93 | | | |
| 35 | γE-C(octyl)-βA | 30 | 60 | 90 | 2200 | 1100 | 500 |
| 36 | γE-C(p-cyanoBz)-G | 80 | 70 | 90 | 250 | 550 | 500 |
| 37 | γE-C(t-Bu)-G | 88 | 74 | 90 | | | |
| 38 | γE-C(p-BrBz)-G | 60 | 50 | 90 | 1000 | 1140 | 300 |
| 39 | γE-C(Bz)-G | 26 | 53 | 84 | | | |
| 40 | γE-C(p-t-BuBz)-G | 49 | 51 | 82 | 2000 | 950 | 200 |
| 41 | γE-C(Bz)-A | 40 | 30 | 80 | | | |
| 42 | γE-C(Hx)-A | 8 | 30 | 80 | | | |
| 43 | γE-C(Me-I) (Bz)-βA | 10 | 20 | 80 | 2000 | 2000 | 30 |
| 44 | γE-G-C(Hx)-φG | 30 | 45 | 7 | | | |
| 45 | γE-C(Cu)-G | 38 | 25 | 74 | 3000 | 1500 | 400 |
| 46 | γE-C(Pr)-A | 13 | 46 | 62 | ND | 900 | 800 |
| 47 | γE-C(neopentyl)-G | 35 | 36 | 62 | 3000 | 1200 | 300 |
| 48 | γE-C(p-FBz)-G | 10 | 40 | 60 | 20000 | 3800 | 640 |
| 49 | γE-C(Pr)-D | ND | 33 | 49 | | | |
| 50 | γE-C(Pr)-V | 12 | 15 | 28 | | | |
| 51 | γE-C(Bz)-H | 4 | 2 | 8 | 25000 | 25000 | 10000 |

Abbreviations as in Table 1 and text above, except: Conc.=Concentration; ND =not detected; IC$_{50}$=Inhibitor Concentration causing 50% reduction in activity; Bu=butyl; t-Bu=tert-butyl; Cu=cumyl (α, α-dimethylbenzyl); IMe= iodomethyl; γE-α-aminooctanoic-G (cmpd 8)=γE-C(Hx)-G with C(Hx) replaced by an analog lacking sulfur; G-γE-C (octyl)-G (cmpd 14)=additional G at N-terminus of γE-C (octyl)-G; cyclic=N and C termini the tripeptide are covalently linked (peptide bond); γE-G-C(Hx)-φG (cmpd 44)=an additional G is inserted between G and C in γE-C (Hx)-φG.

Within Table 5 the paralogs are grouped by human GST isoenzyme selectivity, and within each selectivity class they are ranked by decreasing potency. Paralogs that showed strong selectivity for the P1—1 and M1a—1a isozymes were clearly identified in this survey, but no new selective inhibitor for A1—1 was found beyond those previously described. The criteria set for proceeding to screening beyond the test of inhibition at the 1-mM concentration were: inhibitions of >90% on any GST isozyme or a >6-fold difference in inhibition between an isozyme pair. The IC$_{50}$ value for those paralogs meeting the initial criteria are also presented in Table 5.

A more accurate measure of the binding of paralogs to GST isozymes is obtained by means of GSH competition experiments to determine a K$_i$ value. Such tests were performed on those compounds that had IC$_{50}$ potencies in the 10- to 100-μM range or exhibited >5-fold selectivities between isozymes, and for which >90% pure compounds had been made. If the inhibition by the paralog is competitive, then the K$_m$ values for GSH in the presence and absence of inhibitor can be used to determine the K$_i$ value, or dissociation constant, between the paralog and the GST isozyme. The IC$_{50}$ values were used to establish an appropriate concentration of inhibitor to yield a roughly 50 inhibition at 1 mM GSH. Data obtained in the GSH competition experiment with various paralogs were plotted in a Hanes-Woolf plot. Parallel lines of the inhibited and non-inhibited conditions in a Hanes-Woolf plot indicates that the paralog interacts with the GST-active site. For most combinations of paralog and GST, strict parallelism was observed. The K$_m$ value obtained for GSH alone in this entire series of experiments ranged between 0.4 and 0.6 mM, which was approximately 10-100 orders of magnitude weaker than that recorded for the most potent paralog.

Table 6 presents the K$_i$ values for this subset of interesting compounds.

TABLE 6

Inhibition of human GST activity by purified GST paralogs: micromolar K$_i$ conc. determined by competition binding with GSH

| | K$_i$ Values | | | |
|---|---|---|---|---|
| Structure | α | μ1-1 | μ2-2 | π |
| γE-C(Hx)-G | 0.84 | 2.0 | 36.0 | 10.0 |
| γE-C(Hx)-φG | 5.8 | 41.0 | 97.0 | 0.85 |
| γE-C(Hx)-βA | 43.0 | 11.0 | 42.0 | 550.0 |
| γE-C(Bz)-βA | 360.0 | 22.0 | 26.0 | 710.0 |

TABLE 6-continued

Inhibition of human GST activity by purified GST paralogs: micromolar $K_i$ conc. determined by competition binding with GSH

| Structure | $K_i$ Values | | | |
|---|---|---|---|---|
| | α | μ1-1 | μ2-2 | π |
| γE-C(Bz)-φG | 20.0 | 25.0 | 31.0 | 0.45 |
| γE-C(p-MeBz)-βA | 43.0 | 2.1 | 20.0 | 40.0 |
| γE-C(p-ClBz)-φG | 10 | 11 | 16 | 0.09 |

Most of these compounds appeared more potent in these studies than in the original screening tests because the new preparations used for the GSH competition experiments were at least 90% pure. A further contribution comes from the arithmetic definition of $IC_{50}$ as compared with $K_i$; the values are equal only as both the GSH and the CDNB concentrations approach zero, which was not the case in the present standard protocol. With regard to specificity, the more accurate determinations were generally consistent with the preliminary data, although in several cases relative preferences were changed.

Quantitative Structure/Activity Relationships

Following standard medicinal chemistry procedures, trends were sought in the quantitative structure/activity relationship (QSAR) of these compounds. For this purpose, a series of n-alkyl derivatives of GSH were tested. Results of a detailed exploration of this feature is summarized in Table 7.

TABLE 7

Inhibition of GST activity by S-(n-alkyl)-GSH adducts; micromolar concentration required for 50% inhibition

| S-(n-alkyl)-GSH | | GST isozyme | | |
|---|---|---|---|---|
| C number | Name | P1-1 | A1-1 | M1a-1a |
| C1 | Methyl | 1,000 | 2,500 | 1,300 |
| C2 | Ethyl | 750 | 1,800 | 650 |
| C3 | Propyl | 500 | 900 | 100 |
| C4 | Butyl | 200 | 140 | 20 |
| C5 | Pentyl | 100 | 10 | 5.0 |
| C6 | Hexyl | 80 | 2.0 | 3.0 |
| C7 | Heptyl | 20 | 1.5 | 1.5 |
| C8 | Octyl | 10 | 1.5 | 1.5 |
| C9 | Nonyl | 1.5 | 1.0 | 1.0 |
| C10 | Decyl | 0.75 | 1.0 | 0.75 |

Abbreviation: C = Compound

These results show, first, that the inhibitory potency of the compounds increases with the chain length of the n-alkyl group and, second, that this parameter does not generate a regular trend in isozyme selectivity. It is striking that the results obtained for the paralog compounds presented in Table 5 show a much greater diversity in the pattern of inhibition than do those obtained for the set of n-alkyl derivatives of GSH presented in Table 7.

Numerous small organic molecules have also been previously reported to inhibit GST activity (Mannervik, B., et al., CRC Crit Rev Biochem (1988) 23:283-337), although only a few have been carefully characterized with respect to isolated human isozymes. Since comparisons of these compounds with the radically different peptide-based structures were expected to be useful for a more detailed QSAR study, testing of such compounds also was undertaken. Several of these compounds showed potency and selectivity comparable to those of the peptide-based compounds. The results are summarized in Table 8.

TABLE 8

Inhibition of GST activity by nonpeptide (small organic) compounds; micromolar concentration required for 50% inhibition

| | | GST isozyme | | |
|---|---|---|---|---|
| Abbreviation | Compound | P1-1 | A1-1 | M1a-1a |
| cb | Cibacron blue | 0.4 | 4.0 | 1.5 |
| dx | Doxorubicin | 700 | 80 | 500 |
| ea | Ethacrynic acid | 4.0 | 2.0 | 3.0 |
| gs | Gossypol acetic acid | 200 | 4.0 | 4.0 |
| hm | Hematin | 1,000 | 2.0 | 5.0 |
| rb | Rose bengal | 8.0 | 0.5 | 1.0 |
| sp | Sulfobromophthalein | 20 | 25 | 5.0 |
| in | Indomethacin | >600 | 300 | >600 |
| eb | Eosin b | 4.0 | 2.5 | 2.0 |
| ey | Eosin y | 3.5 | 5.0 | 30 |

Graphical Analysis of Inhibition Data

The multidimensional inhibition data (each axis representing the extent of inhibition for one of the recombinant GSTs) were analyzed on an IBM-compatible personal computer (PC) by the principal-components algorithm in Pirouette, a multivariate statistical software package developed for chemical data by Infometrix, Inc. (Seattle, Wash.). The principal components are the eigenvectors of the covariance matrix with the largest associated eigenvalues. As such, they represent composite parameters derived from the original axes to satisfy two conditions: (1) the principal components are independent (orthogonal) dimensions, and (2) they account for the largest portion of the variance in the data set. Consequently, projection of data onto a plane defined by principal components maximizes the clarity of visualization by spreading the data out along dimensions of maximal scatter. Points that are close together in such a projection thereof faithfully display correlations in the original higher-dimensional space. Target values are also plotted that represent postulated ideal compounds with 100-fold specificity factors and 0.1-μM $K_i$ values. For this analysis, inhibition potency was defined as log ($1/IC_{50}$), or log $1/K_i$) when this more accurate value was available.

FIG. 1 presents a graphical analysis of $IC_{50}$ data from Tables 5, 7 and 8 combined with the $K_i$ data in Table 6. To determine this plot, inhibition properties were first plotted in a three-dimensional space whose axes represent the extent of inhibition for each of the three recombinant isozymes. The principal components of the data distribution were then determined (Massart, D. L., et al., Chemometrics: a textbook (1988), Elsevier, Amsterdam). In simple terms, principal components are composite factors, derived from the original axes, that are mathematically optimized to display correlations in a multivariate data set by plotting points along axes chosen to maximize scatter. The plot shown is a projection of the data onto the plane defined by the second and third principal components. The first principal component is a dimension largely representing potency, and scatter in this property is well displayed in the tables. Choosing the second and third principal components for FIG. 1 highlights the specificity factor, which is believed to be an equally important aspect of quality. Such a multivariate plot allows convenient inspection of the quality (both potency and selectivity) of the tested reagents. Also indicated in the plot are target properties defined as 100-fold specificity and 0.1-μM $K_i$.

The multivariate analysis of the potencies and selectivities of the inhibitors that is presented in FIG. 1 highlights several other interesting features as well. First, it indicates that the benzyl/phegly paralog (compound 4, Table 5) comes rather close to the goal of a P1—1-specific inhibitor. Second, the benzyl/β-ala (compound 30), 4-methylbenzyl/βala (compound 29), and cyclic benzyl/phegly (compound 31) paralogs are the most selective for the M1a—1a enzyme but do not come as close to the goal as achieved for the P1—1 enzyme. Third, no novel A1—1-selective paralog was discovered in this survey.

The analysis of small organic molecules shows that a variety of potencies and specificities are also available from this class of chemical structures. Many of the most effective of such compounds are extremely hydrophobic dyes, however, and are thus unlikely to be clinically useful due to high background binding to proteins in general. Although competition experiments with these inhibitors have not yet been done to determine directly whether they are competitive inhibitors, work is in progress to convert them into GSH derivatives with the hope of achieving potency and selectivity greater than those available from the compounds described in this paper.

In the design of more effective inhibitors, the data analysis by multivariate statistics, as summarized in FIG. 1, should be particularly useful for defining structural trends. Finally, the empirically observed trends visualized in this way should provide useful insights for comparison with structural data on GSTs, including studies using X-ray crystallography, high-resolution nuclear magnetic resonance (NMR), and site-directed mutagenesis.

Pharmacological Implications

The diversity of GST activity in tumors, both qualitatively and quantitatively, represents a significant therapeutic opportunity for targeting existing chemotherapy drugs preferentially to tumors. The same diversity, however, poses a major challenge to the pharmaceutical chemist in that potency alone is not sufficient for utility; selectivity among a group of closely related enzymes is also needed. The paralog approach of this invention is well suited to such a challenge. As demonstrated in the present work, crude ligands are useful as initial probes (Table 5). Reliable assessment of inhibitory properties, however, requires about 50 mg of purified compounds (Table 6). Systematic sampling is thus a very useful strategy for limiting the characterization work to a reasonable level.

Furthermore, the range of structures sampled contributes directly to QSAR and enzyme-structure correlation studies aimed at identifying features responsible for isozyme selectivity and for potency. For example, all but one of the most selective inhibitors for the M1a—1a isozymes have beta-alanine as the C-terminal amino acid in the GSH moiety of the paralog. Both of the most selective inhibitors for the P1—1 isozyme have phenylglycine as the C-terminal amino acid of the GSH moiety.

The best inhibitors obtained in this study show the same potency range as the previously studied inhibitor hexyl GSH, which is the standard ligand used for affinity purification of GST isozymes. The potency of these inhibitors is also similar to or better than that of ethacrynic acid, which is being tested clinically as a drug to potentiate chemotherapy, and this observation suggests that these novel inhibitors may also be useful for the potentiation of chemotherapy. For instance, preferential expression of P1—1 has been reported in a range of tumors, and a potentiator based on the P1—1 selective inhibitor benzyl/phegly (compound 4) may thus be useful in cancer therapy.

Among the paralogs identified by this screen for which a $K_i$ value had been determined (Table 6), all showed competitive inhibition with GSH indicating that they are targeted to the active site of the GST isozymes for their effect and, thus, that they should affect the activity of GST against substrates other than CDNB. A variety of alkylating agents are substrates for GST, and isozymes differ significantly in their specificity for these substrates. Differential expression of particular isozymes in individual tumors may therefore account for variability in responsiveness to treatment. This problem may be overcome by application of appropriate paralogs of this invention, first, to determine GST isoenzyme complements of individual tumors, thereby to identify acceptable cytotoxic agents least susceptible to the predominant GST isozymes of a given tumor and, second, to provide paralog inhibitors offering the greatest potentiation of a selected drug by inhibition of whatever GST activity is still present against that drug.

For inhibition of GST isozyme activities in living cells, for instance to potentiate cytotoxic drugs, the inhibitors identified in this example require modifications according to the present invention, to enhance permeation of the cell membrane, as described above and exemplified in Example 11, below.

EXAMPLE 10

Use of the Compounds of the Invention in HPLC Affinity Chromatography of Human Liver GSTs This example describes a rapid method for the determination of the glutathione S-transferase (GST) isoenzymes, for instance, in human liver, using a new HPLC affinity support. Liver cytosol is injected directly onto an HPLC column (0.46×5 cm) containing a support with a covalently bound affinity ligand (S-octyl glutathione) specific for the isoenzymes. Contaminating cytosolic proteins are removed in a washing step. The isoenzymes are eluted with a linear gradient of a different affinity ligand in the mobile phase. Coinciding with the affinity ligand gradient, a salt gradient (0–200 mM sodium chloride) is applied. In this manner the isoenzymes are fractionated into the enzymatically active homodimers and heterodimers. The monomeric and dimeric composition of the fractionated isoenzymes are determined by SDS-PAGE, ELISA and reversed-phase chromatography. For one liver three Alpha class isoenzyme subunits, forming three heterodimers and two homodimers, are detected. Five livers are analyzed and the homodimer A1—1 is found to be the predominant glutathione S-transferase isoenzyme. Minor amounts of Pi and Mu class isoenzymes are also detected. This nondenaturing high performance affinity chromatography method reduces analysis time by a factor of ten when compared to other affinity analysis methods for the glutathione S-transferases.

One available chromatographic method for the separation of a range of glutathione S-transferases (GSTs) in a dimeric, active form is affinity chromatography using isocratic and/or gradient elution with a counter ligand. This method combines the purification of the GSTs from the cytosol by affinity chromatography with a separation of the individual GSTs. Resolution of GST homodimers and heterodimers has previously been accomplished using this technique with either S-hexyl glutathione or glutathione as the affinity ligand bound to agarose. Due to the large particle diameter and slow flow rates inherent with agarose gels, the fractionation time for these studies was approximately 25 h (Hayes, J. D., et al. (eds.), Glutathione S-Transferases and Drug Resistance, Taylor and Francis, London, 1989, p. 17) which explains why this technique is not used for the routine analysis of GSTs. An HPLC column containing immobilized glutathione as the affinity ligand has been described for the preparative purification of GSTs (LeCreta, F. P., et al., J Chromatog (1988) 434:83–93), but no attempt was made to separate the individual isoenzymes.

This novel HPLC method of this invention uses a stationary phase with a GST affinity ligand (e.g., S-octyl glutathione) covalently linked to HPLC particles packed into an analytical HPLC column.

Affinity matrix. The synthesis of the affinity matrix follows the general procedure of Sundberg and Porath (*J Chromatoqr* (1974) 90:87). HEMA (hydroxyethyl methacrylate) BIO 1000, 1,4-butanediol diglycidyl ether and 0.6M sodium hydroxide containing 2 mg/ml of sodium borohydride (0.03/1/1, w/v/v) were mixed overnight. The particles were filtered and washed with water, ethyl alcohol and acetone. To 700 mg of the dried particles were added S-octyl glutathione (75 mg) dissolved in 3.5 ml of 0.5M sodium carbonate. The suspension was mixed for approximately 90 h. After filtration the particles were washed with (i) 1M sodium chloride, 0.1M sodium phosphate (pH 9), (ii) 1M sodium chloride, 0.1 sodium acetate (pH 4.5), (iii) water, (iv) ethyl alcohol and (v) acetone.

Packing of HPLC columns. The affinity material (650 mg) was slurried in 20 ml of water and was packed at high pressure into stainless steel columns 0.46×5 cm. (Supelco Co., Bellefonte, Pa.). The column frits were 2 μm (average pore diameter) titanium encased in a CTFE ring (Upchurch Scientific, Oak Harbor, Wash.). A Haskell (Burbank, Calif.) DSTV-122 liquid pump was used to provide the drive solvent (water) during the packing process. The columns were packed at 2000 psi with 50 ml of water and then 4000 psi with 50 ml of water.

A significant saving in GST analysis time was achieved by performing the separation on the novel HPLC packing described here. Liver samples were analyzed in 2 hours, more than ten times faster than similar separations using Sepharose-6B based affinity supports. Washing and eluting steps were significantly shorter in duration with the HPLC method. In the analysis of five human livers (Table 9, below) advantage was taken of the pressure stability of the HPLC matrix by conducting the washing step at 1.5 ml/min. Flow rates of at least 2 ml/min can be tolerated in this system with no loss of affinity bound GST isoenzymes.

The high resolution affinity separation of the GST isoenzymes described here depended upon the simultaneous application of two concentration gradients. One gradient consisted of a linearly increasing concentration of either a glutathione paralog, for instance TER106 (i.e., γE-C(Bz)-βA), or S-butyl glutathione, both of which are known competitive inhibitors of the GSTs (see Example 9, above). In the loading step, a GST complexes with an affinity ligand covalently linked to the stationary phase. As the concentration of the competitive inhibitor (TER106 or S-butyl glutathione) increases during the elution step, the GST increasingly partitions into the mobile phase and finally elutes.

The order of elution of a mixture of GSTs is a complex function of their affinities for both the immobilized affinity ligand and the competitive inhibitor in the mobile phase. For instance a change in elution order was observed when comparing the difference in GST elution profiles using two different eluting ligands. Elution with S-butyl glutathione as compared with elution with TER106 shifted the Mu class isoenzyme to a broad, longer retained peak relative to the Alpha class peaks. In addition, the S-butyl glutathione elution resulted in the coelution of Ax-y and Ay-y which were resolved with TER106 elution. Twice the concentration of TER106 to S-butyl glutathione was needed to produce similar chromatographs, reflecting their differing affinities for the isoenzymes.

The second gradient was a salt gradient which was applied coincident with the ligand gradient. Without this gradient the first three peaks coeluted. Thus this separation depended on both an affinity gradient and a salt gradient. The salt gradient may be acting to overcome ionic interactions between the proteins and the stationary phase bound affinity ligand, S-octyl glutathione, which was expected to have a net negative charge at pH 6.0.

The recovery of CDNB conjugating activity eluted with an affinity ligand from the affinity column averaged 76% for three livers while the average yield of total activity (affinity ligand eluted activity plus unretained activity) was 83%. The yield of CDNB conjugating activity from the affinity column described here was comparable to that described in previous reports using other systems.

The proportion of unretained activity for three livers varied from 3% to 13%. To insure that the fraction of unretained activity was not due to a system problem such as column saturation, portions of cytosol from the same liver (L005N) were processed in five consecutive chromatographic runs. The fraction of unretained activity averaged 2.7% with high and low values of 3.5% and 2.3%. From this it was concluded that the variation of unretained activity for different liver samples was a characteristic of the liver sample.

The identities of GST isoenzymes in the major peaks were identified by SDS-PAGE electrophoresis, ELISA and reversed-phase HPLC. Liver L006N appears to contain three forms of Alpha subunits. The reversed-phase chromatogram of the GSTs isolated from liver L006 shows two peaks which elute after A1. These later eluting proteins tentatively have been designated as subunits Ax and Ay, based on further subunit analyses.

For the analysis of human livers, S-butyl glutathione was chosen as the eluting ligand because it separated Mu class GSTs from the Alpha class. In addition livers other than L006N had only A1 or in some cases A1 plus only one of the Ax or Ay subunits so that the complete separation of the Alpha class dimers afforded by TER106 was not required. The five human livers were analyzed for GST dimeric content by affinity chromatography and for monomeric content by reversed-phase chromatography (Table 9).

TABLE 9

Affinity and Reversed-Phase Analysis of Human Liver

| | Affinity Separation[1] | | | | |
|---|---|---|---|---|---|
| Liver | P1-1 | Ax-y Ay-y | A1-y | A1-x | A1-1 | M1b-1b |
| L006 | minor[2] | + | + | + | + | minor |
| L007 | minor | + | + | − | + | − |
| L004 | minor | + | − | + | + | minor |
| L005 | minor | − | − | minor | + | + |
| L002 | — | − | minor | − | + | minor |

| | Reversed-Phase Separation | | | | |
|---|---|---|---|---|---|
| | P1 | M1b | A1 | Ax | Ay |
| L006 | minor | minor | + | + | + |
| L007 | minor | − | + | − | + |
| L004 | minor | minor | + | + | minor |
| L005 | minor | minor | + | minor | minor |
| L002 | minor | minor | + | − | minor |

[1]Affinity Chromatography Buffers; A,10 mM Sodium Phosphate (pH 6.0); B, 200 mM Sodium Chloride in A; C, 20 mM S-Butyl Glutathione in B. Conditions: 0–5 min, A, 0.1 ml/min; 5–21 min, B, 1.5 ml/min; 21–34 min, A, 1 ml/min; 34–35 min, A, 0.1 ml/min; 35–155, 0–42% C, 0.1 ml/min.
[2]Symbols: +, Greater than 10% of total peak area; minor, Less than 10% of total peak area; −, Not detected.

The amount of cytosol injected onto the affinity column was equivalent to approximately 20 mg of liver. In previous reports the predominant forms of GST in human liver were A1 monomers and A1—1 dimers. This was the case for the five livers examined here. When Ax or Ay subunits were detected in appreciable amounts the corresponding heterodimers were also found. For L007N which had appreciable amounts of monomer Ay, both the homodimer Ay-y and the heterodimer A1-y as well as A1—1 were detected. Human liver L005N which had Ax but only a minor amount of Ay exhibited A1-x and A1—1 but no Ax-x was detected as in the case of L006N. Minor amounts of P1 were detected by reversed-phase analysis in all five samples and were also detected by affinity analysis in four of the five livers. Previous investigations also show Pi to be a minor component in human liver. Small amounts of the Mu class GSTs were detected by the reversed-phase method. Due to poor peak shape in affinity chromatography, the detection of the Mu class is difficult when it constitutes only a minor portion of the total GST content.

This new affinity chromatography system using HPLC technology has significant advantages over conventional soft gel affinity systems for the analysis of the GST dimeric content of tissues. The time of analysis is reduced by a factor of ten. In addition the sensitivity for this affinity system is greater because the peak volumes for HPLC affinity are only about 0.5 milliliter compared to 50–100 milliliters when using conventional soft gels. This technique also has the advantage of combining both sample cleanup and analysis into a single step. Other techniques such as reversed-phase HPLC, chromatofocusing or electrophoresis require a separate affinity step to batch purify the GSTs before the final analysis.

Affinity chromatography using gradients of a counter ligand in the eluent is a powerful separation technique. Variation of the biospecific ligand in the eluent results in chromatographic separations exhibiting different selectivities. The different selectivities observed are due to the unique set of binding constants that exist among ligands in their associations with various isoenzymes. This was the case for the GSTs when comparing elution profiles using TER106 or S-butyl glutathione as the counter ligand. Many more compounds of the present invention, as well as other ligands, interact with GSTs, and any of these could give a unique separation allowing a custom separation to be developed. In particular, the analytical methods reported here can be readily scaled up for preparative isolation of particular GSTs of interest.

EXAMPLE 11

Use of the Compounds of the Invention in Potentiation of Cytotoxic Agents in Human Cells This example describes potentiation in human tumor cells of a cytotoxic agent currently used in cancer chemotherapy by GST inhibitors including compounds of the present invention, as well as enhanced intracellular efficacy of esterified forms of these compounds.

HT-29 (human colon adenocarcinoma) cells were obtained from Dr. Roberto Ceriani (Cancer Research Fund of Contra Costa County, Walnut Creek, Calif.) and were used in log phase of growth unless otherwise specified. Chlorambucil (CMB) was obtained from Sigma (St. Louis, Mo.) and was dissolved in 100% ethanol. All GST inhibitors were dissolved in ethanol, DMSO, or water just prior to use. The same amount of solvent added to culture medium served as the vehicle control.

In a modified clonogenic assay for cytotoxicity, cells were suspended at $2 \times 10^5$ cells/ml in serum-free medium in the presence of vehicle or inhibitor. Inhibitors were used at concentrations that resulted in $\geq 90\%$ survival when compared to vehicle treated cells. Cells were incubated for 2 hours, then varying doses of CMB were added. At the end of a second 2-hour incubation, cells were diluted to 7.5–10× $10^3$/ml in serum- containing medium and plated in quadruplicate at 200 µl/well in Microtest III microtiter plates.

Plates were incubated for 6 days and assayed by a modified methylene blue method. Briefly, cells were fixed with 1.25% glutaraldehyde in PBS then stained with 0.05% methylene blue in distilled water. Plates were washed several times in distilled water to remove unretained dye and retained dye was resolubilized in 0.03 N HCl. Plates were read at 650 nm in a Molecular Devices Vmax plate reader (Molecular Devices, Redwood City, Calif.). $IC_{50}$ values (inhibitor concentration causing 50% reduction in cell viability) were determined for the drug in the presence or absence of inhibitor from dose-response curves. A dose modification factor (DMF), a measure of potentiation of cytotoxicity, was calculated for each inhibitor by dividing the $IC_{50}$ value of CMB without inhibitor treatment by the $IC_{50}$ value for CMB with inhibitor treatment.

Results of potentiation tests with several GST inhibitors in HT29 cell cultures are summarized in Table 10.

TABLE 10

Potentiation of Chlorambucil Cytotoxicity in Human Cells by GST Inhibitors and Their Esters

| | | Parent Compound | | Diethyl ester | |
|---|---|---|---|---|---|
| GST Inhibitor | (No.)[a] | Dose tested[b] (µM) | DMF[c] | Dose tested[b] (µM) | DMF[c] |
| γE-C(octyl)-φG | (9) | N.D. | — | 5 | 0.86 ± 0.02 |
| γE-C(Hx)-φG | (6) | 100 | 1.1 ± 0.02 | 12.5 | 1.27 ± 0.02 |
| γE-C(Bz)-φG | (4) | 100 | 1.08 ± 0.01 | 12.5 | 1.65 ± 0.04 |
| γE-C(naphthyl)-G | — | 200 | | 12.5 | 1.21 ± 0.01 |

[a]Number of compound in Table 5, Example 9, above.
[b]Test dose was determined fromn toxicity curve and analogs were used at the dose at which ≥90% survival occurred in the presence of the analog alone.
[c]Dose modification factor. Values are mean ±S.D. of 2–3 experiments.

The results in Tables 10–12 show that several GSH analogs found to be inhibitors of GSH, as shown in Example 9, Table 5, also potentiate killing of human tumor cells in culture by CMB which is a substrate for various GSTs. Further, as shown in Table 10, this potentiation is greatly enhanced by esterification which is designed to enhance uptake of the GST inhibitors. Thus, γE-C(Bz)-φG (compound 4, Table 5) at 100 µM did not enhance cell killing by CMB, reducing the concentration CMB needed for 50% cell killing by a DMF of 1.08. In contrast the diethyl ester of compound 4 at only 12.5 µM enhanced CMB cytotoxicity by a factor of 1.65.

Preferential expression of P1—1 has been reported in a range of human tumors. In the present study the efficacy of CMB potentiation of the several GST inhibitors tested correlated directly with their potencies as inhibitors of the human π-class GST isoenzyme, P1—1, as shown in Table 11.

TABLE 11

Rank Correlation of Chlorambucil Dose Modification Factors of GST Inhibitors with $K_i$ value for Inhibition of Human GST P1-1

| Rank Inhibitor order | No.[a] | Relative Ki value of parent compound | Rank order | DMF[b] of DEE |
|---|---|---|---|---|
| γE-C(Bz)-φG | (4) | 1 | 1 | 1.651 |
| γE-C(Hx)-φG | (6) | 2.1 | 2 | 1.272 |
| γE-C(naphthyl)-G | — | 3 | 3 | 1.213 |
| γE-C(octyl)-G | (9) | 4.8 | 4 | .864 |

[a]Number of compound in Table 5, Example 9, above.
[b]Dose modification factor of diethyl ester. Values are mean ± S.D. of 2–3 experiments.

The effect of esterification or amidation of the compounds of Formula (1) on their potentiation of chlorambucil and HT-29 cells was also determined. The chlorambucil and HT-29 cells was also determined. The dose modification factor was determined for the diethyl ester, the diamide, and the ester/amide of γE-C(Bz)-φG at relevant concentrations. The diester showed 1.65±0.04 modification of chlorambucil toxicity at 12.5 μM; the diamide showed 1.0 modification in a single experiment at 200 μM; the ester/amide hybrid showed a modification of 1.45±0.16 at 50 μM concentration. The results for the diethyl ester and the ester/amide hybrid are given as the mean ±SD of three experiments.

Octyl G and Benzyl PG were tested in a standard clonogenic assay using three cell lines: HT4-1, a subclone of HT-29; SKOV-3 an ovarian carcinoma, and VLB, a vinblastine-resistant variant of SKOV-3. Three chemotherapeutic drugs, chlorambucil, adriamycin and mitomycin C were used as the toxic agents. In these assays, the cells were seeded at 300 cells/well in 2 ml of medium in 6-well plates in the presence of the compounds of the invention as the diethyl esters. The compounds were used at concentrations that resulted in more than 85% survival when compared to controls. After incubation for 1–2 hours to permit cells to attach, varying doses of the chemotherapeutic agents were added. At least three replicate wells were plated for each test condition and the plates were incubated for two weeks. Colonies were fixed in 95% ethanol and stained with crystal violet for colony counting. $IC_{50}$ values were determined for the chemotherapeutic agent in the presence or absence of the compound of the invention and dose modification factors were calculated by dividing the $IC_{50}$ value of drug without the invention compound by the $IC_{50}$ value of the drug with the invention compound. The modification factors obtained in each protocol are shown in Table 12.

TABLE 12

Ability of selected GSH analogs to potentiate drug toxicity as demonstrated in a clonogenic assay

| Cell Line | GSH Analog | DMF[a] for Chlorambucil | Adriamycin | Mitomycin C |
|---|---|---|---|---|
| HTR-1 | Diethyl ester of benzyl PG (25 μM) | 3.28 | 1.2 | n.d.[b] |
|  | Diethyl ester of octyl G (5 μM) | 1.74 | 1.13 | 1.56 |
| SKOV-3 | Diethyl ester of benzyl PG (25 μM) | 1.24 | 1.14 | 1.03 |
|  | Diethyl ester of octyl G (2.5 μM) | 1.03 | 1.24 (@5 μM)[c] | n.d.[b] |
| VLB | Diethyl ester of benzyl PG (25 μM) | N.D.[d] | 2.5 | .82 (@5 μM)[c] |
|  | Diethyl ester of octyl G (5 μM) | N.D.[d] | 1.06 | 1.63 |

[a]Dose modification factor.
[b]No data due to toxicity of analog.
[c]Test dose was different from listed at the left.
[d]Not determined.

As shown in the table, significant modification was obtained when chlorambucil was used as the drug versus HT4-1 cells in the presence of 25 μM of the diethyl ester of benzyl PG. Significant modification was also achieved in VLB cells when treated with adriamycin in the presence of 25 μM of the same compound.

Figure 2:
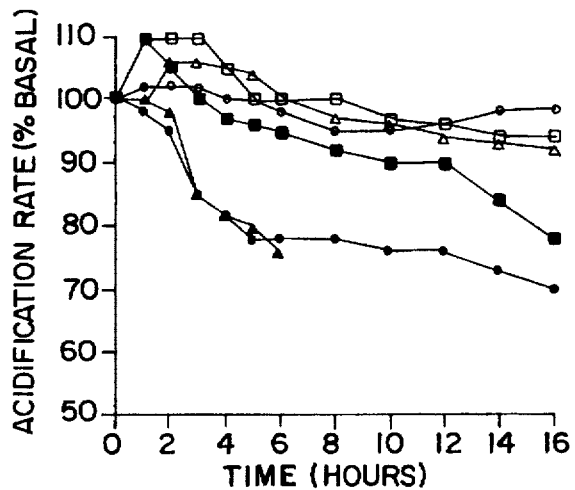
FIG. 2a demonstrates that the diester form is helpful for cell penetration.
FIG. 2b is a graph showing the effect of the diethyl ester of benzyl-PG (γE-C(Bz)-φG see below) on the potentiation of chlorambucil.

FIG. 2a illustrates the results for varying dosages of chlorambucil and the modifying effect of 25 μM of the diethyl ester of benzyl PG. The open squares (□) represent chlorambucil alone, the closed circles (●) chlorambucil in the presence of the invention compound. As seen in FIG. 2a, the survival rate is markedly diminished when the invention compound is added. FIG. 2b confirms that the diethyl ester is necessary to penetrate the cells. HT4-1 cells were tested for survival in the presence of either benzyl PG (closed squares, ■) or its diethyl ester (closed circles, ●). Unesterified diethyl G has substantially no effect on these cells while the diethyl ester is clearly toxic.

EXAMPLE 12

Metabolic Effects of the Invention Compounds

The metabolic effects of the compounds of the invention on HT-29 cells, related to toxicity were tested using a Cytosensor Microphysiometer made by Molecular Devices, Inc., Menlo Park, Calif. and described in McConnell, H. M. et al. Science (1992) 257:1906–1912 and by Wada, H. G. et al. AATEX (1992) 1:154–164. Changes in pH of the culture medium are measured as a function of cellular metabolism. Acidification rates of the small volume of liquid flowing over the cells correlate with the number of live cells in the reaction chamber; a reduction of acidification rate reflects reduced numbers of surviving cells.

In this illustration, HT-29 cells were plated at $4 \times 10^5$ cells/chamber in a medium containing 10% fetal calf serum. After 16–18 hours the serum level was reduced to 1% and the cells were maintained for another 18 hours. Cells were then exposed to either ethacrynic acid (50 μM), the diethyl ester of benzyl PG (20 μM) or a vehicle (0.1% ethanol) for 4 hours. The medium was then replaced with serum-free low buffer capacity medium and Microphysiometer analysis was initiated. Half of the chambers were exposed to 100 μM chlorambucil and the other half to vehicles (0.1% ethanol). Acidification rates were monitored for 16 hours and the data are expressed as percentage of the basal (100%) acidification rates.

Figure 3:
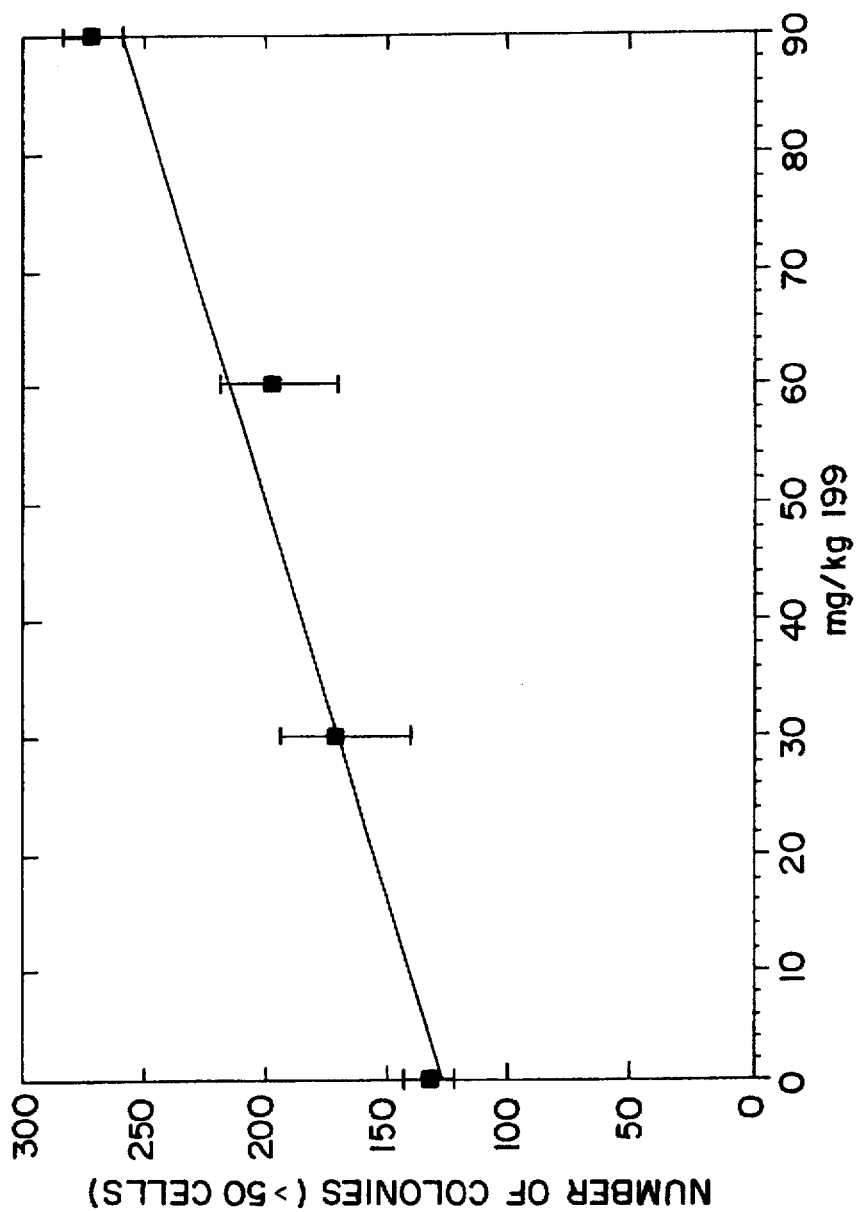
FIG. 3 shows the effect of ethacrynic acid and benzyl-PG on chlorambucil toxicity in HT-29 cells.

The results are shown in FIG. 3. Neither the diethyl ester of phenyl PG nor ethacrynic acid alone had any appreciable effect on acidification rates; however, both ethacrynic acid pretreatment and pretreatment with the benzyl PG diethyl ester potentiated the effect of chlorambucil. In the figure, the open symbols reflect no addition of chlorambucil; the closed symbols reflect addition of chlorambucil; the squares reflect the pretreatment with vehicle, triangles pretreatment with ethacrynic acid, and circles pretreatment with benzyl PG diethyl ester.

EXAMPLE 13

GST Analysis of Various Cell Lines

GST profiles of the cell lines used in the foregoing analyses was performed as follows: cells were harvested, washed twice in serum-free medium, washed once in calcium-magnesium-free PBS, and then the pellets snap-frozen and stored at −80° C. The frozen cells were homogenized as described by Castro, V. M. et al. Biochem J (1993) 292:371–377 in 10 mM sodium phosphate, pH 7.0; 0.16 M KCl, 100 μM Pefabloc SC (Central Chem. Inc., Stamford, CT), 1 μM leupeptin (Sigma), 2 mM EDTA and 2 mM dithio-3-itol. The GSTs were isolated from systolic fractions by affinity chromatography using an HPLC column. Reverse-phase analysis of the GSTs on a J. T. Baker 7105–00 Wide-Pore octyl HPLC column (25 cm×4.6 mm, VWR Scientific), protein determinations and determination of CDNB conjugating activity were performed as described by Castro, V. M. et al. Biochem J (1993) 292:371–377. The results are shown in Table 13.

TABLE 13

Reversed-phase HPLC analysis of cytosolic GSTs expressed in tumor cell lines exhibiting drug resistance to alkylating agents

| Cell Line | Percent Total GST Protein | | | | | Total Protein Area[a] | Total CDNB Activity[b] |
|---|---|---|---|---|---|---|---|
| | P1 | A2 | M2 | 33 kD | 27 kD | | |
| HT-29 | 82.4 | 0.9 | 3.0 | 13.7 | — | 1645 | 4996 |
| HT4-1[c] | 83.9 | — | — | 16.1 | — | 1388 | 5021 |
| SKOV-3 | 48.9 | 12.0 | 1.5 | 34.6 | 3.0 | 732 | 2815 |
| VLB[d] | 67.5 | 17.4 | — | 15.1 | — | 1671 | 4757 |

[a]Values are expressed as peak area = mV-sec/mg cystosolic protein.
[b]Values are expressed as mOD/min/mg cytosolic protein.
[c]HT-29 subclone retaining wild type sensitivity to ethacrynic acid.
[d]Vinblastine resistant subclone of SKOV-3.

The results show that all cell lines express P1—1 as a predominant GST isoenzyme. SKOV-3 and VLB cells also express moderate levels of A2—2 but this isoenzyme was found only in trace amounts in HT-29 cells. It was undetectable in HT4-1 cells. Very low levels of MT2—2 were detected in HT-29 and SKOV-3. 33 kD and 27 kD proteins, identified as enoyl Co-A isomerase and GST-M3 respectively, are also found in these cells.

EXAMPLE 14

Stimulation of Bone Marrow Granulocyte Macrophage (GM) Progenitors

The compounds of the invention, when esterified so as to be able to penetrate cells, also stimulate the production of GM progenitors in bone marrow when administered to mammalian subjects. In an illustrative assay, three B6D2F$_1$ mice were treated with various doses of benzyl PG intraperitoneally. Femoral bone marrows were harvested 24 hours later and assayed for GM-CFU by the method of East, C. J. et al. Cancer Chemother Pharmacol (1992) 31:123–126. An increase in the number of colonies in a dose-dependent manner up to a dosage of 90 mg/kg of benzyl PG was obtained. These results are shown in FIG. 4. At 90 mg/kg, approximately 275 colonies/$10^4$ nucleated cells of more than 50 cells were obtained compared to about 140/$10^4$ nucleated cells colonies for controls.

EXAMPLE 15

Potentiation of Melphalan Toxicity in Vivo

Male scid mice were subcutaneously implanted with HT4-1 tumors from donor mice. When tumors reached approximately 100 mm$^3$, the mice were randomized into six treatment groups and treated for seven days as follows:

1. 5 mg/kg melphalan;
2. 10 mg/kg ethacrynic acid;
3. 60 mg/kg diethyl ester of benzyl-PG;
4. 5 mg/kg melphalan +10 mg/kg ethacrynic acid;
5. 5 mg/kg melphalan +60 mg/kg diethyl ester of benzyl-PG;
6 vehicle alone.

The mice were monitored for weight changes and tumor volumes were determined by measurement with calipers. The tumor growth was monitored until the average tumor size reached 1500 mm$^3$ for all groups except melphalan with ethacrynic acid. This group failed to reach this volume even after 72 days.

The results were computed in terms of the tumor volume in the experiment as a percentage of control tumor volume (i.e., in the group administered vehicle alone). In group 1, administered melphalan alone, the tumors were approximately 75% of the volume of controls. In group 5 when the diethyl ester of benzyl-PG was administered along with the melphalan, the tumor volume mean was approximately 55% of control. For group 4 administered a combination of melphalan and ethacrynic acid, the volumes were approximately 35% of control. Thus, both ethacrynic acid and diethyl ester of benzyl-PG potentiate the effects of melphalan. (The volume measurements were taken at the time control tumors reached 1500 mm$^3$.)

We claim:

1. A method to stimulate the production of granulocyte macrophage progenitors in the bone marrow of a subject which method comprises administering to said subject an effective amount of a compound of the formula:

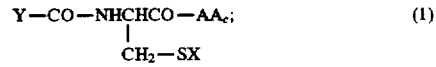

$$Y-CO-NHCHCO-AA_c; \quad (1)$$
$$\qquad\qquad |$$
$$\qquad\qquad CH_2-SX$$

or an amide, ester or mixed amide/ester thereof,
wherein X is a hydrocarbon radical optionally substituted on any aromatic moiety contained therein selected from the group consisting of hexyl, heptyl, octyl, benzyl and naphthyl; Y—CO is γ-Glu or β-Asp and AA$_C$ is an amino acid selected from the group consisting of phenylglycine and β-alanine.

2. The method of claim 1 wherein Y—CO is γ-Glu.

3. The method of claim 1 wherein the ester is a diester which is the diethyl ester.

4. A method to stimulate the production of granulocyte macrophage progenitors in the bone marrow of a subject which method comprises administering to said subject an effective amount of a diester of a compound selected from the group consisting of γ-glutamyl S-octyl cysteinyl glycine;

γ-glutamyl S-hexyl cysteinyl glycine;

γ-glutamyl S-octyl cysteinyl phenylglycine; and

γ-glutamyl S-benzyl cysteinyl glycine.

5. A method to stimulate the production of granulocyte macrophage progenitors in the bone marrow of a subject which method comprises administering to said subject an effective amount γ-glutamyl S-benxzyl cysteinyl phenylglycine-diethyl ester.

* * * * *